(12) United States Patent
Porter et al.

(10) Patent No.: US 6,991,919 B1
(45) Date of Patent: Jan. 31, 2006

(54) BIOCHEMICAL SYNTHESIS APPARATUS

(75) Inventors: Neil Porter, Enfield (GB); Frances Mary Giaquinto, Enfield (GB)

(73) Assignee: Biodiversity Limited, (GB)

( * ) Notice: Subject to any disclaimer, the term of this patent is extended or adjusted under 35 U.S.C. 154(b) by 0 days.

(21) Appl. No.: 09/936,726

(22) PCT Filed: Mar. 17, 2000

(86) PCT No.: PCT/GB00/01000

§ 371 (c)(1),
(2), (4) Date: Jan. 2, 2002

(87) PCT Pub. No.: WO00/55297

PCT Pub. Date: Sep. 21, 2000

(51) Int. Cl.
*C12P 1/00* (2006.01)
*C12P 1/04* (2006.01)
*C12P 1/02* (2006.01)
*C12P 7/14* (2006.01)

(52) U.S. Cl. .................. 435/41; 435/170; 435/171; 435/162

(58) Field of Classification Search .............. 435/41, 435/170, 171, 162, 163, 283.1
See application file for complete search history.

(56) References Cited

U.S. PATENT DOCUMENTS

| 2,761,813 A | | 9/1956 | Goetz |
| 2,923,669 A | | 2/1960 | Poitras |
| 3,448,011 A | | 6/1969 | Russomanno |
| 4,145,254 A | * | 3/1979 | Shepherd et al. ........... 435/132 |
| 4,772,558 A | * | 9/1988 | Hammann ................ 435/304.2 |
| 4,859,586 A | | 8/1989 | Eisenberg et al. |
| 4,868,123 A | * | 9/1989 | Berson et al. ........... 435/286.6 |
| 5,013,564 A | * | 5/1991 | St. Martin et al. .......... 426/250 |
| 5,122,470 A | | 6/1992 | Banes |
| 5,215,920 A | | 6/1993 | Lyman |
| 5,324,657 A | | 6/1994 | Tanny |
| 5,879,932 A | | 3/1999 | Van Erdecoyk et al. |

FOREIGN PATENT DOCUMENTS

| DE | 839 245 | 5/1952 |
| EP | 0 236 751 | 9/1987 |
| EP | 0 390 367 | 10/1990 |
| EP | 0 581 022 | 2/1994 |
| FR | 2 070 560 | 9/1971 |

OTHER PUBLICATIONS

Kikkoman Corp., "Membrane Surface Liquid Culture Fermenter for Microbes and Plane," Patent Abstracts of Japan of JP 08-089231, (1996).

* cited by examiner

*Primary Examiner*—Susan Coe
*Assistant Examiner*—Randall Winston
(74) *Attorney, Agent, or Firm*—Finnegan, Henderson, Farabow, Garrett and Dunner, L.L.P.

(57) ABSTRACT

A biochemical synthesis apparatus comprises a receptacle for containing a medium, and a support on which a microorganism can be placed. The support can be placed in contact with the medium, so as to allow access of the microorganism to the medium. The support with the microorganism can be removed from the medium, allowing the medium to be replaced. By this, the receptacle can firstly contain a growth medium, and secondly a secondary medium capable of causing the production by the microorganism of a potentially useful biochemical.

14 Claims, 26 Drawing Sheets

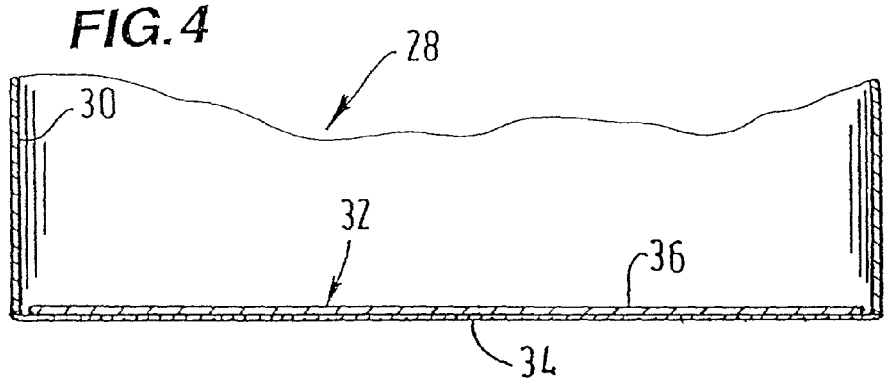
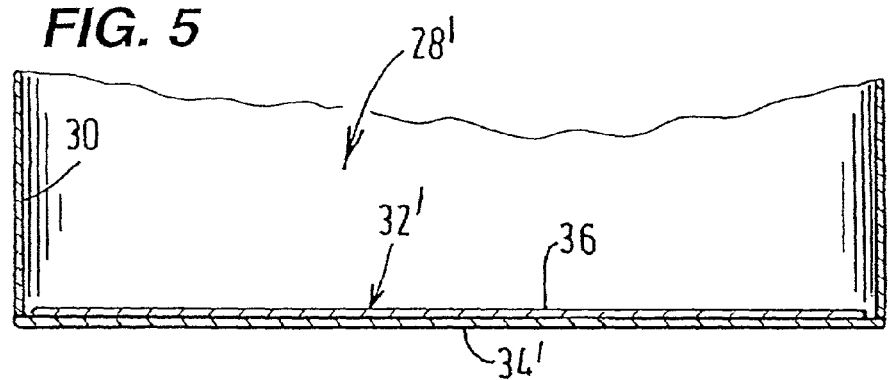
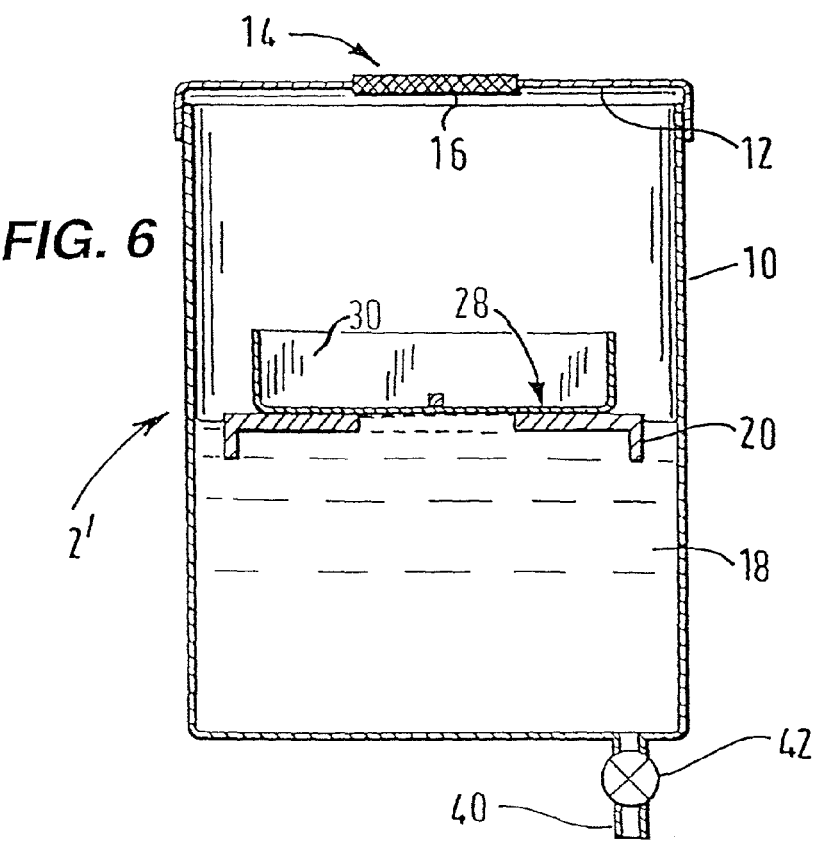

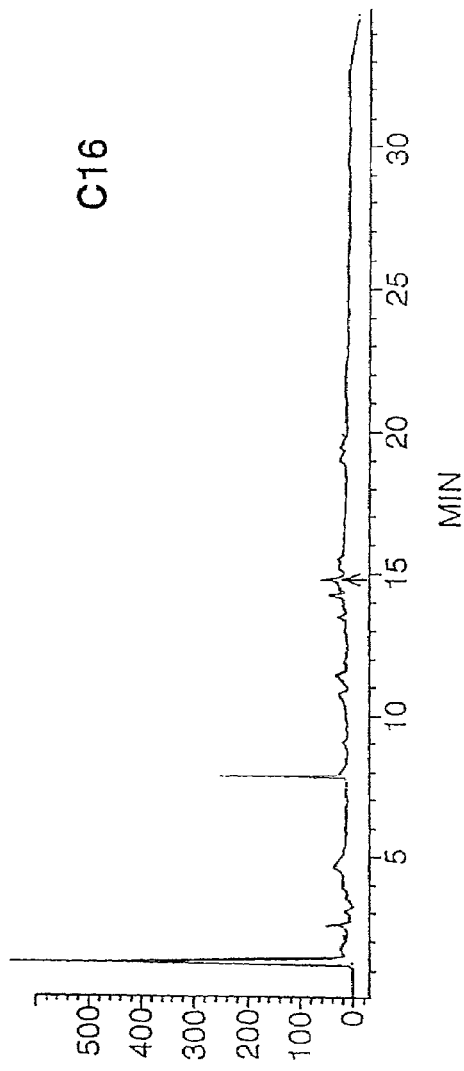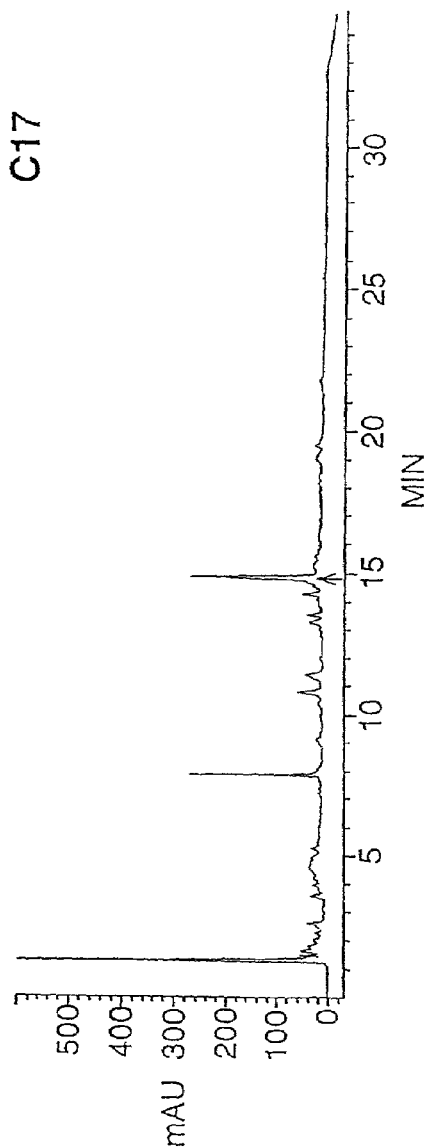
FIG. 9a
FIG. 9b

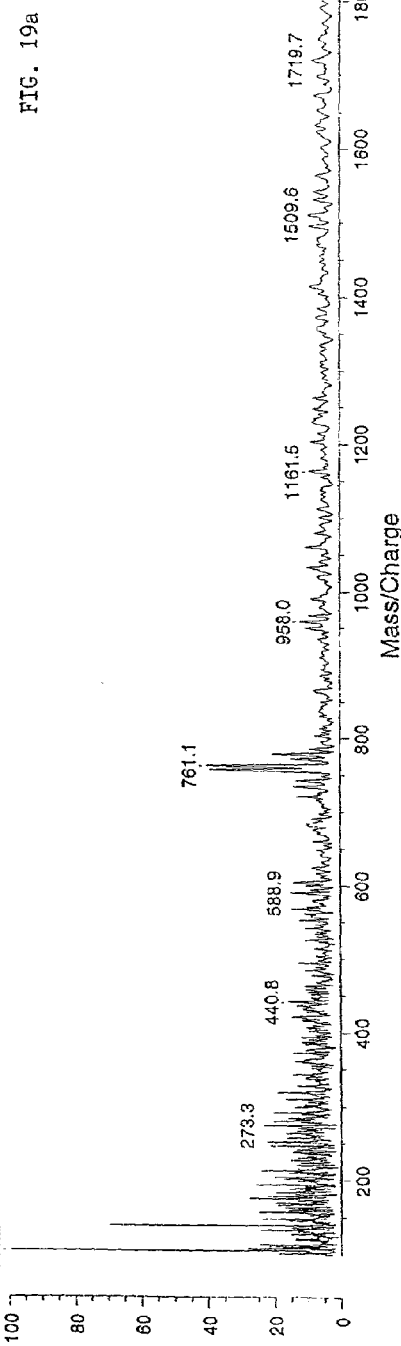
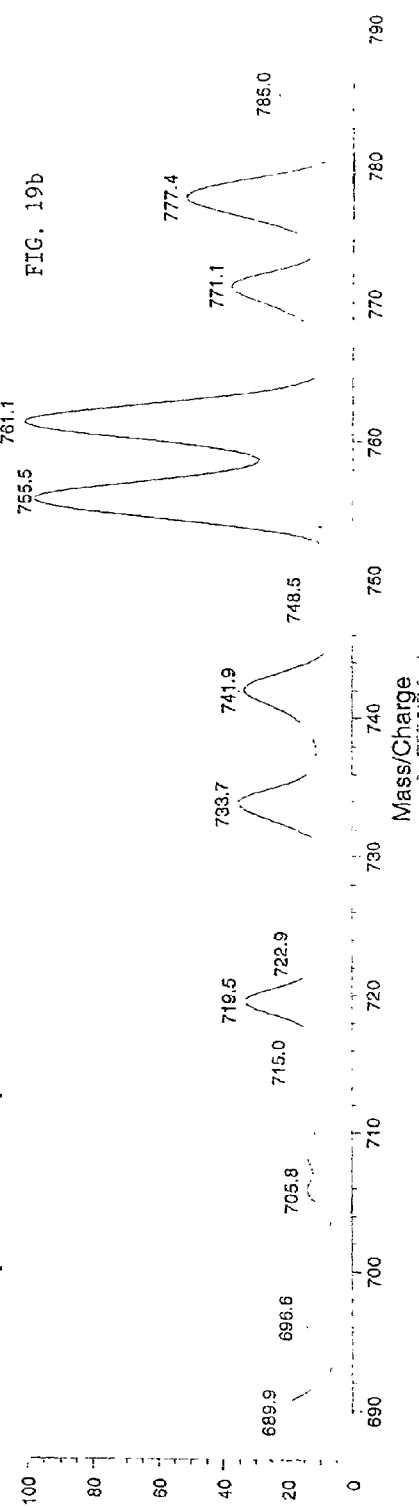
FIG. 19a
FIG. 19b

BIOCHEMICAL SYNTHESIS APPARATUS

The present invention is concerned with apparatus for use in a biochemical reaction of a microorganism, and a process for the synthesis of one or more biochemicals as a result of that biochemical reaction.

Microorganisms such as fungi and bacteria produce a vast diversity of chemical species through biochemical pathways which constitute secondary metabolism. Secondary metabolism commences in the absence of one or more nutrients essential to the performance of primary metabolism. While primary metabolites and their metabolism are essential for growth, secondary metabolites by definition are not, but they are believed to contribute to the survival of a microorganism in a number of ways, as set out in "Diversity of Microbial Products—Discovery and Application" by N. Porter and F. M. Fox (1993), Pesticide Science 39, pp 161–168. Secondary metabolites, therefore, often exhibit diverse biological properties and as such can provide the basis of new therapeutic drugs.

As a consequence, microorganisms are constantly being studied with a view to finding new and useful secondary metabolites. However, commonly used processes for the fermentation and production of samples containing secondary metabolites are often not compatible with the requirements of modern drug screening technologies. In small scale fermentations, secondary metabolism cannot be controlled effectively and many different and often randomly selected nutrient solutions must be used to achieve the specific set of conditions required for secondary metabolism. Additionally, secondary metabolites secreted by the microorganism are diluted and contaminated with complex nutrients present in the growth medium. This can lead to low quality samples for screening.

In liquid fermentation, secondary metabolites are currently produced by suspending a sample of the microorganism in a medium consisting of an aqueous solution or suspension of a combination of appropriate nutrients. The suspension is placed in a stoppered flask which allows the ingress of oxygen and the flask is agitated by shaking to mix and aerate the suspension. Growth and primary metabolism of the microorganism occurs until one of the essential nutrients in the medium is exhausted, at which point secondary metabolism commences.

Initially, after inoculating the nutrient medium with microorganism there is often a variable delay or lag period before growth commences. Then, in trophophase, the organism grows in a linear or exponential fashion through primary metabolic processes until the growth rate begins to decrease as an essential nutrient, such as nitrogen or phosphate, becomes exhausted as the organism enters idiophase. At that point, secondary metabolism is induced as a result of a specific nutrient exhaustion and a secondary metabolite is produced.

For an individual microorganism, the lag phase can vary due to, amongst other things, the age and size of the culture inoculum. Replicate cultures, while growing at the same rate, could have different lag phases and therefore could finish growing and enter idiophase at different times.

Moreover, different microorganisms could exhibit similar lag phases but differ significantly in their growth rates so that they consume essential nutrients at different rates, and they finish growing at different times, consequently entering idiophase at different times. The different growth rates could also be exhibited by an individual microorganism growing on different nutrient containing media.

For high throughput screening of secondary metabolites, samples thereof need to be generated by cultivating microorganisms in large batches. The inability to control secondary metabolism by established processes means that the potential of each organism within a batch to produce new secondary metabolites is not realised because samples are prepared from fermentations after a fixed time period at which it is expected that secondary metabolism will have commenced. However, for the above reasons organisms may not have begun secondary metabolism. Additionally, secreted secondary metabolites will be mixed with complex nutrients from the growth media. These can interfere with the drug screening procedures, making screening less efficient and productive.

Therefore, it is an object of the present invention to provide apparatus and a procedure which allows more predictable production of secondary metabolite samples in a form compatible with the operational requirements of high throughput screening technologies.

A first aspect of the invention provides a biological procedure including arranging biomass with access to a medium, said medium being suitable to support biomass growth, and replacing said medium with a replacement medium suitable to define conditions for secondary metabolism in said biomass.

A second aspect of the invention provides a procedure for generating a biochemical including the steps of causing an organism to metabolise in the presence of a first medium for growth of biomass and causing said organism to metabolise in the presence of a second medium for generation of said biochemical.

A third aspect of the invention provides a procedure which comprises the steps of growing an organism under conditions of primary metabolism in the presence of excess essential nutrients for growth, separating the organism from the essential nutrients and allowing the organism to metabolise in the absence of essential nutrients under conditions supporting secondary metabolism.

A fourth aspect of the invention provides a procedure which comprises the steps of growing an organism under conditions of primary metabolism in the presence of excess essential nutrients for growth, separating the organism from the essential nutrients and allowing the organism to metabolise in the presence of a reduced concentration of one or more essential nutrients so as to support secondary metabolism.

A fifth aspect of the invention provides a procedure which comprises the steps of growing an organism under conditions of primary metabolism in the presence of excess essential nutrients, separating the organism from the essential nutrients, and placing the organism in conditions supporting secondary metabolism thereby to generate a secondary metabolite.

It is an advantage of the invention that secondary metabolites generated in accordance therewith can be secreted into a liquid medium containing no or limited amounts of defined nutrients but substantially free from the complex mixture of essential nutrients required for the growth of the organism.

It is a further advantage of the invention that defined conditions can be selected to induce and support secondary metabolism in a diverse range of microorganisms.

By providing a specific separation step, the exhaustion of an essential nutrient can be carefully controlled, thereby inducing secondary metabolism and controlling the production of secondary metabolites.

A sixth aspect of the invention provides a biological procedure including placing biomass with access to a medium formulated for biomass growth, selectively removing said biomass from said medium, and placing said biomass with access to a secondary medium suitable to stimulate an alternative metabolic pathway.

A seventh aspect of the invention provides apparatus for arranging a microorganism for metabolism, the apparatus comprising a receptacle for containing a nutrient medium, and a means for supporting a microorganism which allows access to nutrient for metabolism, wherein the means for supporting a microorganism can be selectively separated from the nutrient in use.

An eighth aspect of the invention provides apparatus for supporting biomass such that said biomass can be selectively positioned for access to an environment for controlling a biological process in said biomass in use.

A ninth aspect of the invention provides a procedure including arranging biomass with access to a medium, said medium being suitable to support biosynthesis with respect to said biomass, and replacing said medium with a replacement medium from which a product of said biosynthesis is distinguishable.

Further aspects and advantages of the present invention will be appreciated from the following description of specific embodiments and examples of the invention, with reference to the accompanying drawings in which:

FIG. 4 is a cross-sectional view of the fermentation vessel illustrated in FIG. 3;

FIG. 5 is a cross-sectional view of a fermentation vessel in accordance with a second specific embodiment of the invention;

FIG. 6 is a schematic diagram of apparatus in accordance with a third specific embodiment of the invention;

FIG. 7b is a chromatogram for a control sample illustrated for comparison with the chromatogram of FIG. 7a;

FIG. 9a is a chromatogram for a first test sample prepared in accordance with a third example of a specific method in accordance with the present invention;

FIG. 9b is a chromatogram for a second test sample prepared in accordance with a third example of a specific method in accordance with the present invention;

FIG. 19a is a spectrum generated by mass spectrometry of a sample generated in a sixth example in accordance with the invention;

FIG. 19b is a view of an expanded portion of the spectrum illustrated in FIG. 19a;

FIG. 21b is a view of an exposed portion of the spectrum illustrated in FIG. 21a;

Figure 1:
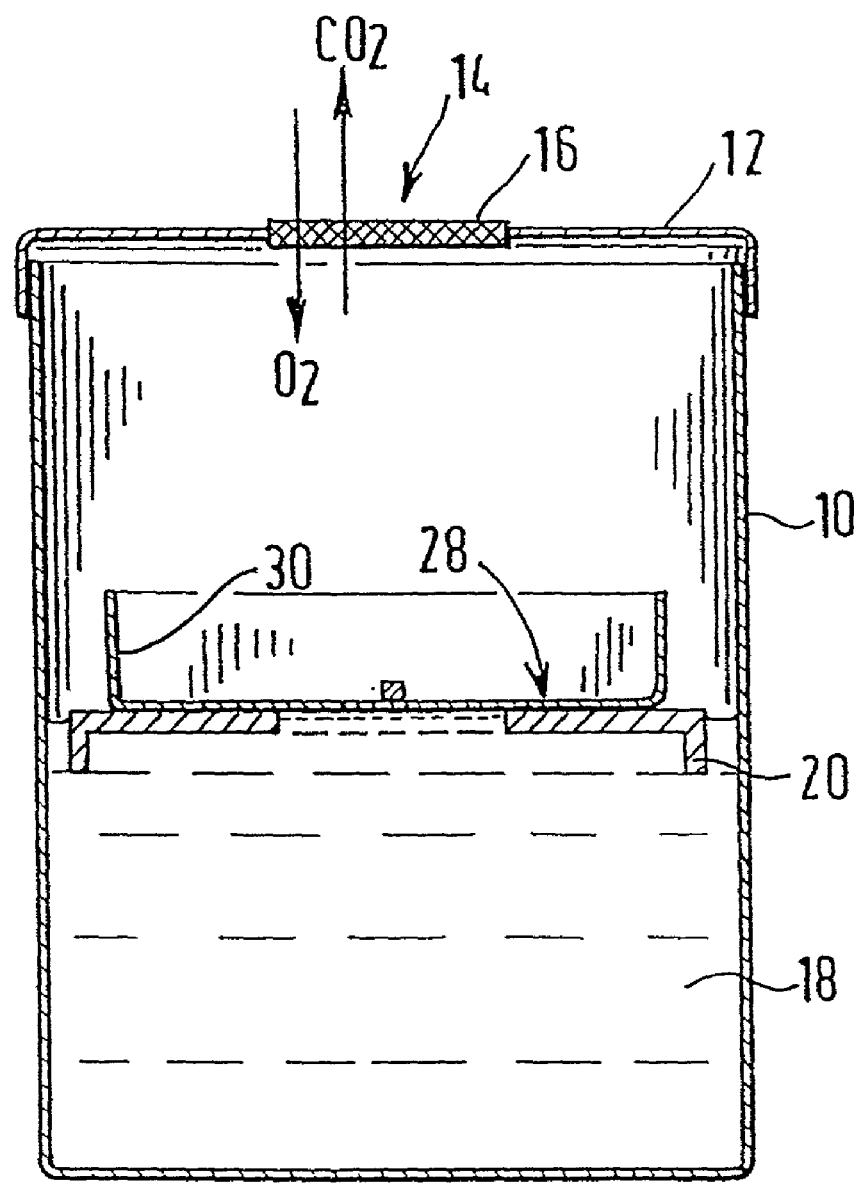
FIG. 1 is a schematic cross-sectional diagram of apparatus in accordance with a first specific embodiment of the invention.

FIG. 1 shows a ferment ation apparatus 2 comprising a fermentation receptacle 10, which is generally cuboidal in shape. The upper end of the receptacle 10 is open, and has a lid 12 fitted thereon. The receptacle 10 and the lid 12 are made of a plastics material capable of withstanding temperatures of up to 121° C. in order to allow for sterilisation thereof in the presence of steam. However, it will be appreciated that other materials, such as stainless steel or glass, would also be appropriate.

The lid 12 has a window 14 including a gas permeable foam insert 16, which allows the transfer of oxygen and carbon dioxide therethrough, as indicated by arrows in FIG. 1.

The receptacle 10 contains an aqueous solution/suspension 18 of a combination of nutrients appropriate to the metabolism of a microorganism to be grown in the fermentation apparatus 2. Particular examples of nutrients and microorganisms will be described later.

Figure 2:
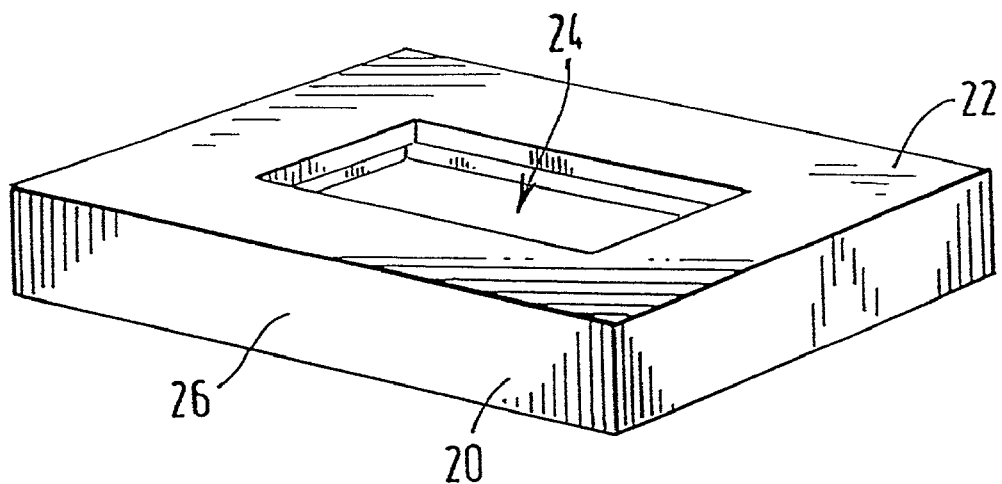
FIG. 2 is a perspective view of a raft of the apparatus illustrated in FIG. 1.

Floating on the surface of the aqueous solution 18 is a raft 20. Accordingly, the volume of the aqueous solution/suspension 18 provided in the receptacle 10 is sufficient to allow flotation of the raft 20. The construction of the raft 20 is best illustrated with reference to FIG. 2. The raft 20 has a generally square laminar body 22 with a square through aperture 24 located centrally therein. A flange 26 extends downwardly as illustrated in FIG. 2 around the periphery of the square body 22.

As illustrated in FIG. 1, the raft 20 is constructed of a material which renders it sufficiently buoyant as to float in the aqueous solution 18, such that the surface of the aqueous solution 18 reaches the level of the square laminar body 22.

Figure 3:
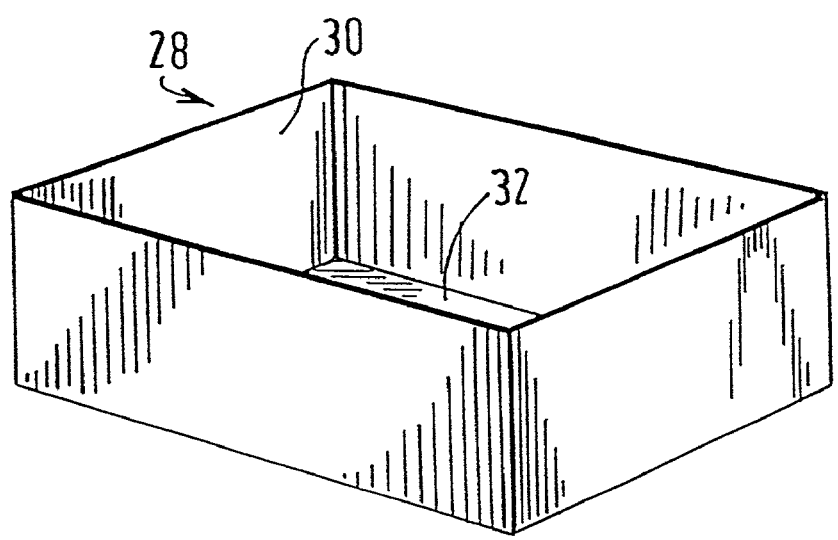
FIG. 3 is a perspective view of a fermentation vessel in accordance with the first specific embodiment of the invention.

A fermentation vessel 28 is placed on the raft 20. The vessel 28, illustrated in FIG. 3, consists of a generally square frame 30 supporting a membrane 32.

FIGS. 4 and 5 illustrate two alternative embodiments of the vessel 28 of different constructions. The first embodiment of the vessel 28 is illustrated in FIG. 4. The membrane 32 of the vessel 28 is constructed of a polypropylene sheet 34 with a pore size of 0.3 micrometers, welded to the frame 30. The polypropylene sheet 34 is treated with a silicone-polyether copolymer to make it water permeable. On the inside (upper) face of the polypropylene sheet 34 is placed a square melt cast polypropylene fibre hydrophilised membrane 36, such as a polypropylene membrane sold as a pre-filter by Millipore Corporation, 80 Ashby Road, Massachusetts, USA.

The solution/suspension held in the receptacle 10 soaks through the polypropylene sheet 34 and is wicked by the membrane 36, so that any microorganism sample inoculated on to the membrane 36 has access to the solution/suspension 18. The soaking through of the solution/suspension can be by means of a pressure gradient derived from the weight of the raft 20 and fermentation vessel 28 in combination.

The second specific embodiment is illustrated in FIG. 5. The vessel 28' is constructed in the same manner as the vessel 28 of the first specific embodiment, except that the membrane 32' thereof has a polypropylene fibre hydrophilised membrane 34', welded to the frame 30, in place of the polypropylene sheet 34.

In the case of the second specific embodiment, since both membranes 34', 36 are hydrophilic, solution/suspension 18 can soak into the membranes 34', 36 by wicking, brought about via capillary action.

A third specific embodiment of the invention is illustrated in FIG. 6. As far as the apparatus 2' of the third embodiment has features corresponding to features in the first and second embodiments, those features are provided with the same reference numerals. The fermentation receptacle 10 of the apparatus 2' includes a drain outlet 40 which is closeable by means of a drain valve 42. In use, liquid contents of the fermentation receptacle 10 can be drained away through the drain outlet 40, which allows the fermentation receptacle 10 to be emptied without lifting and tipping thereof. Whereas the apparatus 2' of the third embodiment of the invention has been provided with a vessel 28 corresponding to the vessel 28 illustrated in FIG. 4, it will be appreciated that the vessel could also take the form of the vessel 28' illustrated in FIG. 5.

Application of the above described first, second and third specific embodiments of the invention will now be described with reference to the following specific examples. The examples involve analysis of two fungi and three actinomycete bacteria.

The microorganisms need to be prepared in order to generate sufficient mycelial growth for investigation. This requires the use of formulated growth media. The present invention allows the use of complex growth media.

Growth media suggested for promoting mycelial growth in fungi include FS and HC4, whose formulations are set out in Tables 1 and 2 below.

TABLE 1

| FS | g/l |
|---|---|
| Sheftone-Z soy peptone | 10 |
| Malt extract, Oxoid L39 | 21 |
| Glycerol | 40 |
| Junlon 110 (Honeywell & Stein) | 1 |
| Adjust to pH 6.3 | |

TABLE 2

| HC4 | g/l |
|---|---|
| Beet molasses, British Sugar | 20 |
| Glycerol | 25 |
| Casein NZ-Amine AS | 7.5 |
| $K_2HPO_4$ (Anhydrous) | 0.3 |
| $CaCO_3$ | 2.5 |
| Tween 80 | 1 ml |

Growth media suggested for promoting mycelial growth in actinomycetes include SV2 and MPGS, whose formulations are set out in Tables 3 and 4 below.

TABLE 3

| SV2 | g/l |
|---|---|
| D-Glucose | 15 |
| Glycerol | 15 |
| Sheftone-Z soy peptone | 15 |
| NaCl | 3 |
| $CaCO_3$ | 1 |
| Adjust to pH 7 | |

TABLE 4

| MPGS | g/l |
|---|---|
| Beet molasses, British Sugar | 20 |
| Sheftone-Z soy peptone | 5 |
| D-Glucose | 10 |
| Sucrose | 20 |
| $CaCO_3$ | 2.5 |

In order to induce secondary metabolism in a microorganism, a culture of the microorganism must be kept in an environment lacking (or having a reduced concentration in) one or more of the nutrients essential to primary metabolism and growth. Therefore, the growth medium selected from the lists set out above must be replaced by a nutrient deficient medium. Several different nutrient deficient media require investigation for each new microorganism, to ensure the identification of the most effective conditions for efficient secondary metabolism. For fungi, the replacement media listed in Table 5 are used in the following examples to investigate secondary metabolism using the apparatus of the specific embodiment of the invention.

TABLE 5

Replacement media

| | |
|---|---|
| 1. | Water |
| 2. | Glucidex (Roquette Frères), 10 g/l |
| 3. | Trehalose, 10 g/l |
| 4. | Glycerol, 10 g/l |
| 5. | Mannitol, 10 g/l |

Water is used as a control, and the other four media contain a source of carbon. For actinomycetes, the replacement media set out in Table 6 are used in the following examples to investigate secondary metabolism using the apparatus of the specific embodiment of the invention.

TABLE 6

Replacement media

| | |
|---|---|
| 1. | Water |
| 2. | Glucidex, 10 g/l |
| 3. | Glucidex, 10 g/l + Praline, 1.5 g/l (C:N is approximately 30:1) |
| 4. | Glycerol, 10 g/l |
| 5. | Glycerol, 10 g/l + Praline, 1.5 g/l (C:N is approximately 30:1) |

Again, water is used as a control. The other four media contain either a source of carbon or a source of carbon and nitrogen. In the case of media 3 and 5 (Table 6), the carbon:nitrogen ratio (C:N) is set at 30:1 to establish conditions which particularly favour secondary metabolism.

Two specific procedures will now be described, for later use in the following examples.

Procedure 1 (Layer Inoculation)

The fermentation apparatus 2 is employed in a first procedure solely for secondary metabolism of a microorganism.

In this case, mycelial growth of the microorganism under investigation is generated in a liquid culture, to serve as an inoculum later referred to as a layer inoculation. This is achieved in a plurality of 250 ml flasks each containing 50 ml growth medium. Each flask is inoculated, in sterile conditions, from microorganism grown on agar slopes, and incubated, with agitation, at 25° C. or 28° C., for 3 to 5 days.

A one liter flask, provided with automatic temperature regulation and stirring devices, is filled with 300 ml of the same growth medium as used in the 250 ml flasks above. This is inoculated with 5% cell culture (about 15 ml) taken from the 250 ml flasks. The vessel is then stirred, using a 45 mm cross-shaped magnetic follower, at 300 rpm and incubated at 25° C. for fungi and 28° C. for actinomycetes. The culture is allowed to grow for up to 5 days, depending on the nature of the microorganism and its growth rate, in order to maintain the culture in growth phase, known as trophophase.

A fermentation apparatus 2 as described above is provided with a vessel 28' as illustrated in FIG. 5. In order to inoculate the apparatus 2, the vessel 28' is temporarily removed from the receptacle of the apparatus 2, and a 50 ml aliquot of the culture contained in the one liter flask is transferred directly to the membrane surface 36. The supernatant is allowed to drain away before the vessel 28' is replaced in the receptacle 10, which contains 60 ml of a replacement medium as described above.

Procedure 2 (Plug Inoculation)

The apparatus 2 is used in a second exemplary method both for the preparation and growth of mycelium of a microorganism for inoculation and for subsequent nutrient secondary metabolism of the microorganism. Apparatus 2 in accordance with the first embodiment is provided as described above with reference to FIGS. 1 to 4 of the drawings. The receptacle 10 of the apparatus 2 is filled with a nutrient solution to a level sufficient to support flotation of the vessel (typically 60–70 ml).

For fungi, a plug of agar taken from the growing edge of a stock Petri dish culture of the microorganism under investigation is deposited on the centre of the membrane 34, 36 of the vessel 28 on the raft 20.

For actinomycetes, inoculation is carried out by placing a spore/mycelial suspension onto the membrane of the vessel 30, the suspension having been prepared from a stock culture of the organism maintained, for instance, on a slope.

The inoculated vessel 30 is retained in the fermentation receptacle 10 for fifteen days, before it is transferred aseptically to a new fermentation receptacle 10 containing 60 ml of a replacement medium as identified above.

Secondary Metabolism

After placement in contact with a replacement medium, fungal cultures are incubated at 25° C., and actinomycete cultures at 28° C., for up to 2 weeks to achieve maximum productivity of secondary metabolites.

Notwithstanding the existence of water as a control replacement medium, control samples are also advisedly established in investigations, in which sample no transfer to a replacement medium takes place. In the case of plug inoculation, a control is established which comprises a fermentation apparatus 2 inoculated with a plug of mycelial growth, which is then left in the same growth medium for the duration of the trials. In the case of layer inoculation, a control is established by transferring mycelial biomass to a vessel 28 and allowing it to drain through. The vessel 28 is then placed in a fermentation receptacle 10 containing the same growth medium as was used to generate the layer inoculation, again for the duration of the trials.

Metabolite Isolation

Secondary metabolite can be produced in the cells of the microorganism under test, in the fermentation broth in which the microorganism resides, or in both. Therefore, samples of both mycelium and filtrate are taken. The mycelium sample is extracted with 10 ml methanol for a minimum of twelve hours, following which the extract is subjected to chromatographic analysis. The broth sample is diluted in suitable HPLC mobile phase, following which it is also subjected to chromatographic analysis. Suitable HPLC conditions will be described for each example outlined below.

Each example outlined below demonstrates the use of the fermentation apparatus of the present invention in the execution of a number of different tasks. The examples demonstrate investigations into the effectiveness of the fermentation apparatus illustrated in FIG. 1, and the method of transferring a microorganism into conditions supporting secondary metabolism, to generate secondary metabolite from five microorganisms treated in a variety of different ways. The five microorganisms investigated in the examples are *Phoma sp.* F16006 and *Trichoderma longibraciatum* 5602E, which are fungi, and *Amycolatopsis orientalis* C2726, *Nocardiopsis sp.* 5997E, and *Streptomyces citricolor* C2778 which are actinomycetes.

Each of the fungi are to be treated in the same manner, likewise the actinomycetes. The microorganisms should be tested under all combinations of available conditions.

In respect of each fungus, twenty fermentation apparata 2 need to be prepared. A first group of five fermentation apparata 2 are prepared with a layer inoculum from a liquid culture generated in FS growth medium and a second group of five with a layer inoculum from liquid culture prepared in HC4 growth medium, in accordance with procedure 1. A third group of five apparata 2 are prepared with plug inoculated cultures grown on FS medium and a fourth group of five apparata 2 with plug inoculated cultures grown on HC4 growth medium, in accordance with procedure 2.

Each receptacle 10 of the five apparata 2 in each group is filled with a respective one of the five replacement media set out in Table 5. The twenty fermentation apparata 2 so inoculated are maintained for ten days before harvest.

Four control apparata 2 are also arranged, two of which are layer inoculated from four day old liquid cultures (one from each of the two available growth media), and the other two of which are inoculated using the plug inoculation technique (from the two available growth media). The fermenting receptacles 10 are filled with corresponding growth media, not replacement media. The apparata are left for fifteen days before harvest for layer inoculated cultures, and twenty five days before harvest for plug inoculated cultures.

Each of the actinomycetes are to be treated in the same general manner, but with some differences in the specific procedures employed. Again, twenty test apparata 2 and four control apparata 2 are assembled, since two growth media SV2, MPGS and five replacement media (Table 6) are available. However, the duration of each stage is in some cases different. In the case of Procedure 1 for actinomycetes, liquid culture for layer inoculation is grown for five days rather than four as per fungi. Incubation after transfer to replacement medium is conducted for ten days rather than the eleven day period set down for fungi. Again, layer inoculum control cultures are grown for 5 days before transfer to apparata 2 containing growth media.

After completion of the relevant incubation period, investigations are put in place to measure the production of metabolite in cell extract and broth extract. In order to measure concentrations of secondary metabolite, the extract under investigation is subjected to HPLC under suitable conditions.

The operating parameters and mobile phase formulations for all examples, except Example B, are set out in Table 7. Chemical standards are used to identify chromatographic peaks corresponding to the secondary metabolites produced by the test organisms.

TABLE 7

| Time (Min) | % Mobile Phase B | Flow (ml/min) |
|---|---|---|
| 0 | 0 | 1 |
| 20 | 100 | 1 |
| 30 | 100 | 1 |
| 32 | 0 | 1 |
| 35 | 0 | 1 |

Mobile Phase A: 5 g/liter sodium lauryl sulphate + 10 ml/liter 0.1M $NH_4H_2PO_4$, pH 2.5.
Mobile Phase B: 75% $CH_3CN$ + 5 g/liter sodium lauryl sulphate + 10 ml/liter 0.1M $NH_4H_2PO_4$, pH 2.5.
Column: Spherisorb 15 cm C5 5 micron.

The conditions for Example B has formulation set out in Table 8.

TABLE 8

| Time (Min) | % Mobile Phase B | Flow (ml/min) |
|---|---|---|
| 0 | 0 | 1 |
| 1 | 0 | 1 |
| 30 | 100 | 1 |
| 35 | 100 | 1 |
| 36 | 0 | 1 |
| 40 | 0 | 1 |

Mobile Phase A: 0.1% TFA.
Mobile Phase B: 75% $CH_3CN$ + 0.1% TFA.
Column: Hypersil 15 cm C18 3 micron.

Finally, standard shaken cultures in accordance with known techniques are also carried out as a comparison of general bioreactor performance. The growth media for these cultures are FS (formulation previously described), SM37, BFMS and K252/P1. The formulations for the latter three media are:

| SM37 | g/l | BFMS | g/l | K252/P1 | g/l |
|---|---|---|---|---|---|
| Lactose | 25 | Arkasoy | 10 | Glucose | 5 |
| $KH_2PO_4$ | 4 | Glucose | 18 | Soluble starch | 30 |
| $CaCO_3$ | 10 | $CaCO_3$ | 0.2 | Arkasoy | 20 |
| Pharmamedia | 20 | $CoCL_2.6H_2O$ | 0.001 | Yeast extract | 5 |
| pH to 6.5 | | $Na_2SO_4$ | 1 | Corn steep liquor | 5 |
| | | Molasses | 18 | $CaCO_3$ | 3 |
| | | Sucrose | 18 | pH to 7.2 | |

The results of the HPLC tests for selected samples produced by the following examples are illustrated as chromatograms in FIGS. 7a and 7b, FIGS. 8a, 8b and 8c, FIGS. 9a, 9b, 9c and 9d, FIGS. 10a, 10b and 10c and FIGS. 11a, 11b and 11c. A chromatogram is a graph of Absorbance (measured in milli Absorbance Units) against retention time (measured in Minutes). Each chromatogram is marked with an arrow pointing at a peak which represents the expected secondary metabolite for that particular sample.

EXAMPLE A

*Phoma sp.* F16006

This fungus produces compound GR 195359. The results of the procedures applied to the microorganism are set out in Table 9.

TABLE 9

| Ref: | Organism | Metabolite | Inoculum Type | Growth Medium | Replacement Medium | Extract Type | Conc (mg/l) |
|---|---|---|---|---|---|---|---|
| TEST | | | | | | | |
| A1 | *Phoma* sp F16006 | GR 195359 | Layer | FS | water | cell | 0 |
| A2 | *Phoma* sp F16006 | GR 195359 | Layer | FS | glucidex | cell | 0 |
| A3 | *Phoma* sp F16006 | GR 195359 | Layer | FS | trehalose | cell | 0 |
| A4 | *Phoma* sp F16006 | GR 195359 | Layer | FS | glycerol | cell | 0 |
| A5 | *Phoma* sp F16006 | GR 195359 | Layer | FS | mannitol | cell | 0 |
| A6 | *Phoma* sp F16006 | GR 195359 | Layer | FS | water | broth | 0 |
| A7 | *Phoma* sp F16006 | GR 195359 | Layer | FS | glucidex | broth | 0 |
| A8 | *Phoma* sp F16006 | GR 195359 | Layer | FS | trehalose | broth | 0 |
| A9 | *Phoma* sp F16006 | GR 195359 | Layer | FS | glycerol | broth | 0 |
| A10 | *Phoma* sp F16006 | GR 195359 | Layer | FS | mannitol | broth | 0 |
| A11 | *Phoma* sp F16006 | GR 195359 | Layer | HC4 | water | cell | 0 |
| A12 | *Phoma* sp F16006 | GR 195359 | Layer | HC4 | glucidex | cell | 0 |
| A13 | *Phoma* sp F16006 | GR 195359 | Layer | HC4 | trehalose | cell | 0 |
| A14 | *Phoma* sp F16006 | GR 195359 | Layer | HC4 | glycerol | cell | 0 |
| A15 | *Phoma* sp F16006 | GR 195359 | Layer | HC4 | mannitol | cell | 246 |
| A16 | *Phoma* sp F16006 | GR 195359 | Layer | HC4 | water | broth | 0 |
| A17 | *Phoma* sp F16006 | GR 195359 | Layer | HC4 | glucidex | broth | 0 |
| A18 | *Phoma* sp F16006 | GR 195359 | Layer | HC4 | trehalose | broth | 0 |
| A19 | *Phoma* sp F16006 | GR 195359 | Layer | HC4 | glycerol | broth | 0 |
| A20 | *Phoma* sp F16006 | GR 195359 | Layer | HC4 | mannitol | broth | 0 |
| A21 | *Phoma* sp F16006 | GR 195359 | Plug | FS | water | cell | 134 |
| A22 | *Phoma* sp F16006 | GR 195359 | Plug | FS | glucidex | cell | 529 |
| A23 | *Phoma* sp F16006 | GR 195359 | Plug | FS | trehalose | cell | 525 |
| A24 | *Phoma* sp F16006 | GR 195359 | Plug | FS | glycerol | cell | 519 |
| A25 | *Phoma* sp F16006 | GR 195359 | Plug | FS | mannitol | cell | 876 |
| A26 | *Phoma* sp F16006 | GR 195359 | Plug | FS | water | broth | 0 |
| A27 | *Phoma* sp F16006 | GR 195359 | Plug | FS | glucidex | broth | 0 |
| A28 | *Phoma* sp F16006 | GR 195359 | Plug | FS | trehalose | broth | 0 |
| A29 | *Phoma* sp F16006 | GR 195359 | Plug | FS | glycerol | broth | 0 |
| A30 | *Phoma* sp F16006 | GR 195359 | Plug | FS | mannitol | broth | 0 |
| A31 | *Phoma* sp F16006 | GR 195359 | Plug | HC4 | water | cell | 0 |
| A32 | *Phoma* sp F16006 | GR 195359 | Plug | HC4 | glucidex | cell | 0 |
| A33 | *Phoma* sp F16006 | GR 195359 | Plug | HC4 | trehalose | cell | 0 |
| A34 | *Phoma* sp F16006 | GR 195359 | Plug | HC4 | glycerol | cell | 0 |
| A35 | *Phoma* sp F16006 | GR 195359 | Plug | HC4 | mannitol | cell | 85 |
| A36 | *Phoma* sp F16006 | GR 195359 | Plug | HC4 | water | broth | 0 |
| A37 | *Phoma* sp F16006 | GR 195359 | Plug | HC4 | glucidex | broth | 0 |
| A38 | *Phoma* sp F16006 | GR 195359 | Plug | HC4 | trehalose | broth | 0 |
| A39 | *Phoma* sp F16006 | GR 195359 | Plug | HC4 | glycerol | broth | 0 |
| A40 | *Phoma* sp F16006 | GR 195359 | Plug | HC4 | mannitol | broth | 0 |
| CONTROL | | | | | | | |
| A41 | *Phoma* sp F16006 | GR 195359 | Layer | FS | FS | cell | 0 |
| A42 | *Phoma* sp F16006 | GR 195359 | Layer | FS | FS | broth | 0 |
| A43 | *Phoma* sp F16006 | GR 195359 | Layer | HC4 | HC4 | cell | 0 |
| A44 | *Phoma* sp F16006 | GR 195359 | Layer | HC4 | HC4 | broth | 0 |
| A45 | *Phoma* sp F16006 | GR 195359 | Plug | FS | FS | cell | 608 |
| A46 | *Phoma* sp F16006 | GR 195359 | Plug | FS | FS | broth | 0 |
| A47 | *Phoma* sp F16006 | GR 195359 | Plug | HC4 | HC4 | cell | 0 |
| A48 | *Phoma* sp F16006 | GR 195359 | Plug | HC4 | HC4 | broth | 0 |
| A49 | *Phoma* sp F16006 | GR 195359 | Shaken | SM37 | | culture | 109 |

In the example, GR 195359 is produced, with two exceptions, on FS medium in cultures inoculated by the plug method. GR 195359 is extracted only from the cell material. The nature of the replacement medium affects the amount of GR 195359 produced by the organism, as demonstrated by test samples A21–A25. In particular, mannitol produces the highest titre of GR 195359 and is able to stimulate production in layer and plug replacement cultures grown on HC4 medium, as shown in samples A15 and A35 respectively. Mannitol stimulates the production of GR 195359 significantly beyond the level achievable in the corresponding control A45 arranged without transfer to replacement medium.

Figure 7A:
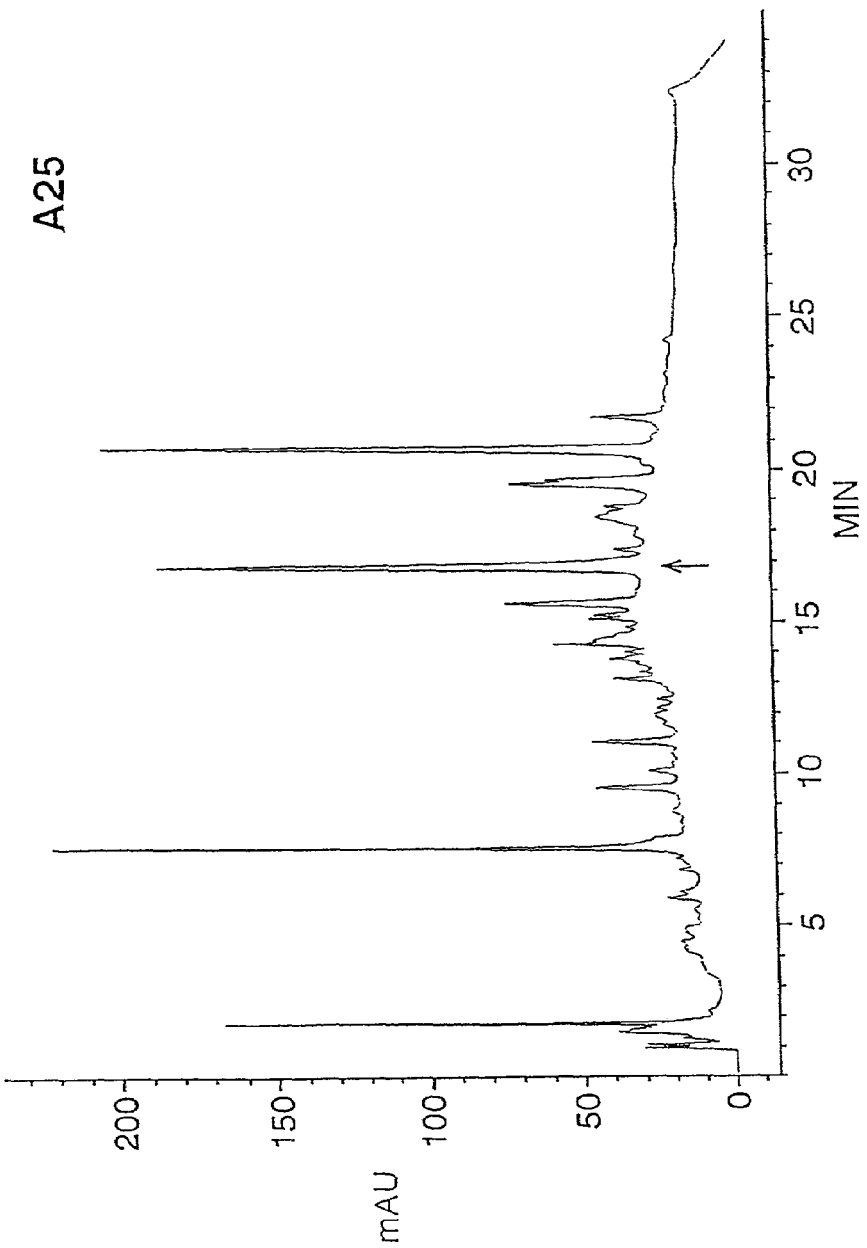
FIG. 7a is a chromatogram for a test sample prepared in accordance with a first example of a specific method in accordance with the present invention.
Figure 7B:
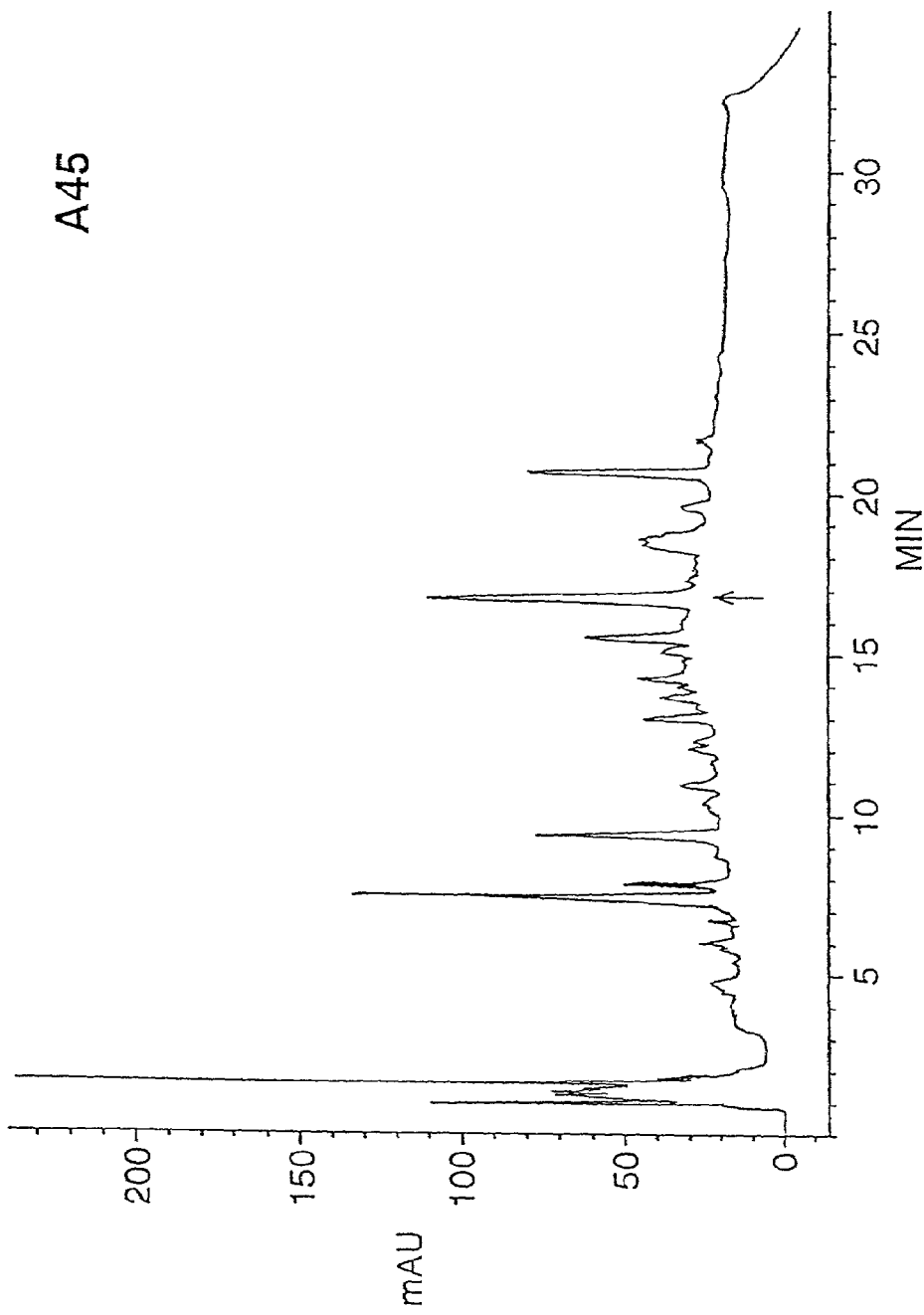

HPLC chromatograms reveal that in cell extracts A21–A25 in respect of which the microorganism has been transferred to replacement medium, the size of the GR 195359 peak relative to the other component peaks is significantly greater than in control samples. This indicates that there is a higher proportion of GR 195359 in cell extracts of replacement cultures. This is illustrated in FIG. 7a, which illustrates sample A25, in comparison with FIG. 7b, which shows its control A45.

Although the titres are not directly comparable, the concentrations of GR 195359 in the described cell extracts are superior to levels in whole culture extracts of *Phoma sp.* F16006 grown in traditional shake flasks on an optimised medium.

EXAMPLE B

Trichoderma longibraciatum 5602E

This fungus produces bisvertinolone. The results of the procedures described above applied to the microorganism are set out in Table 10.

Figure 8A:
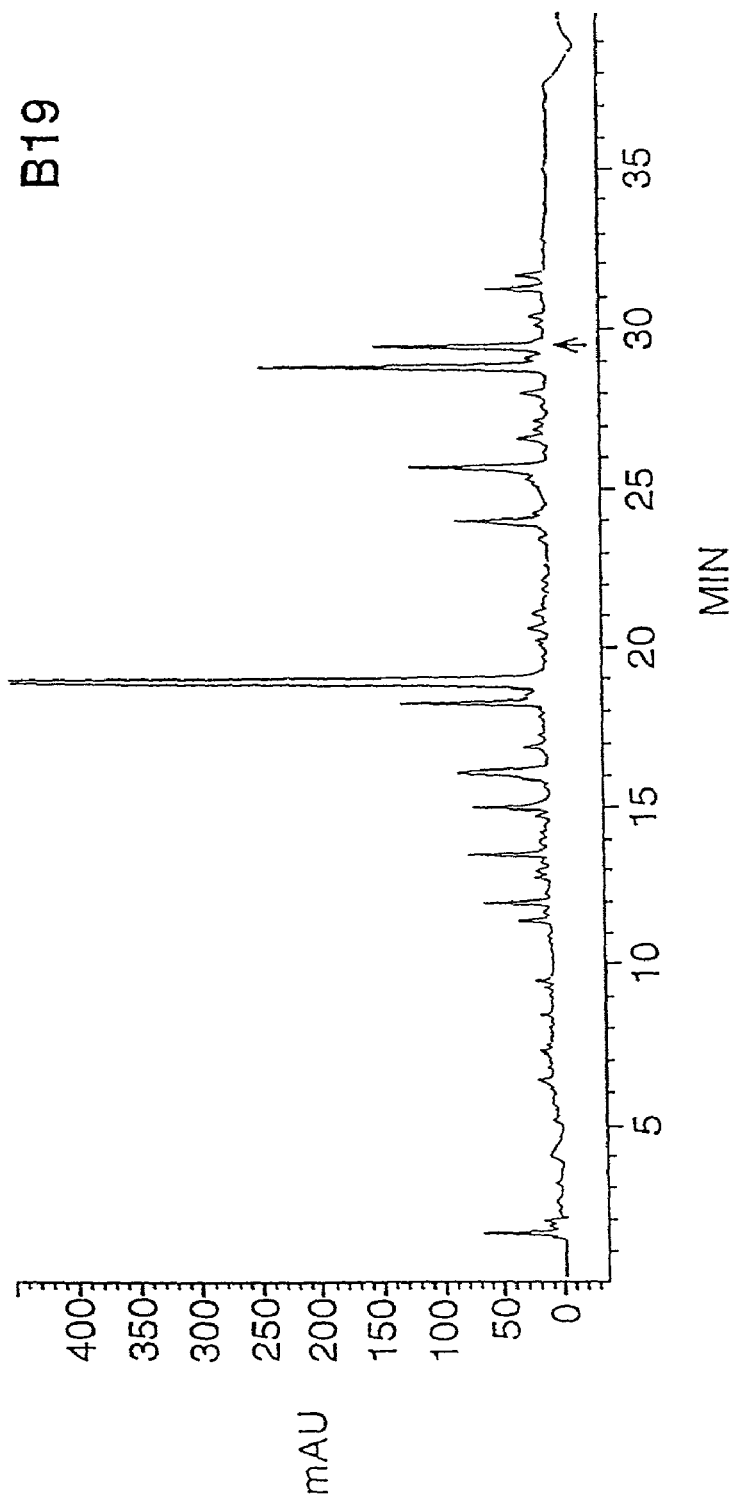
FIG. 8a is a chromatogram for a first test sample prepared in accordance with a second example of a specific method in accordance with the present invention.
Figure 8B:
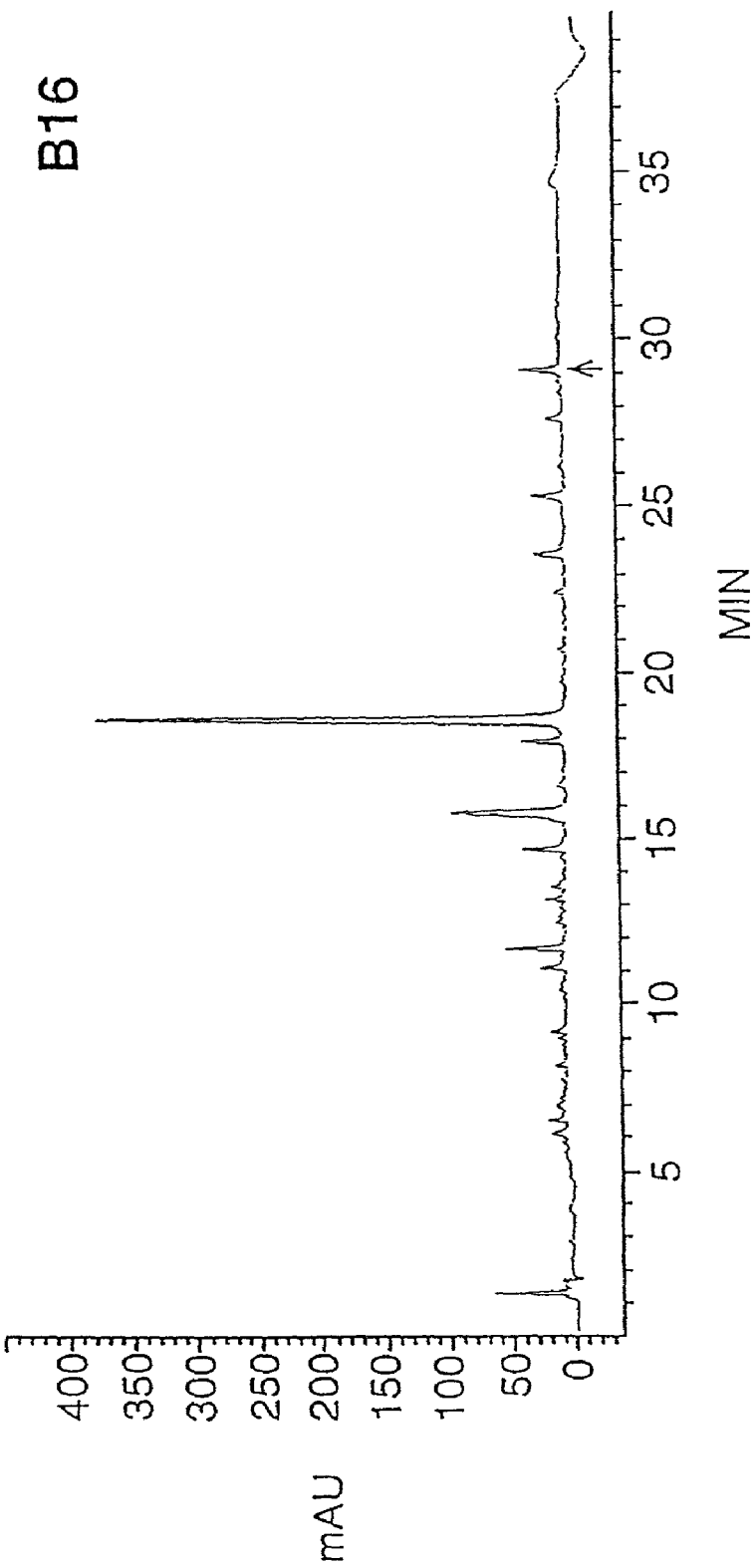
FIG. 8b is a chromatogram for a second test sample prepared in accordance with a second example of a specific method in accordance with the present invention.
Figure 8C:
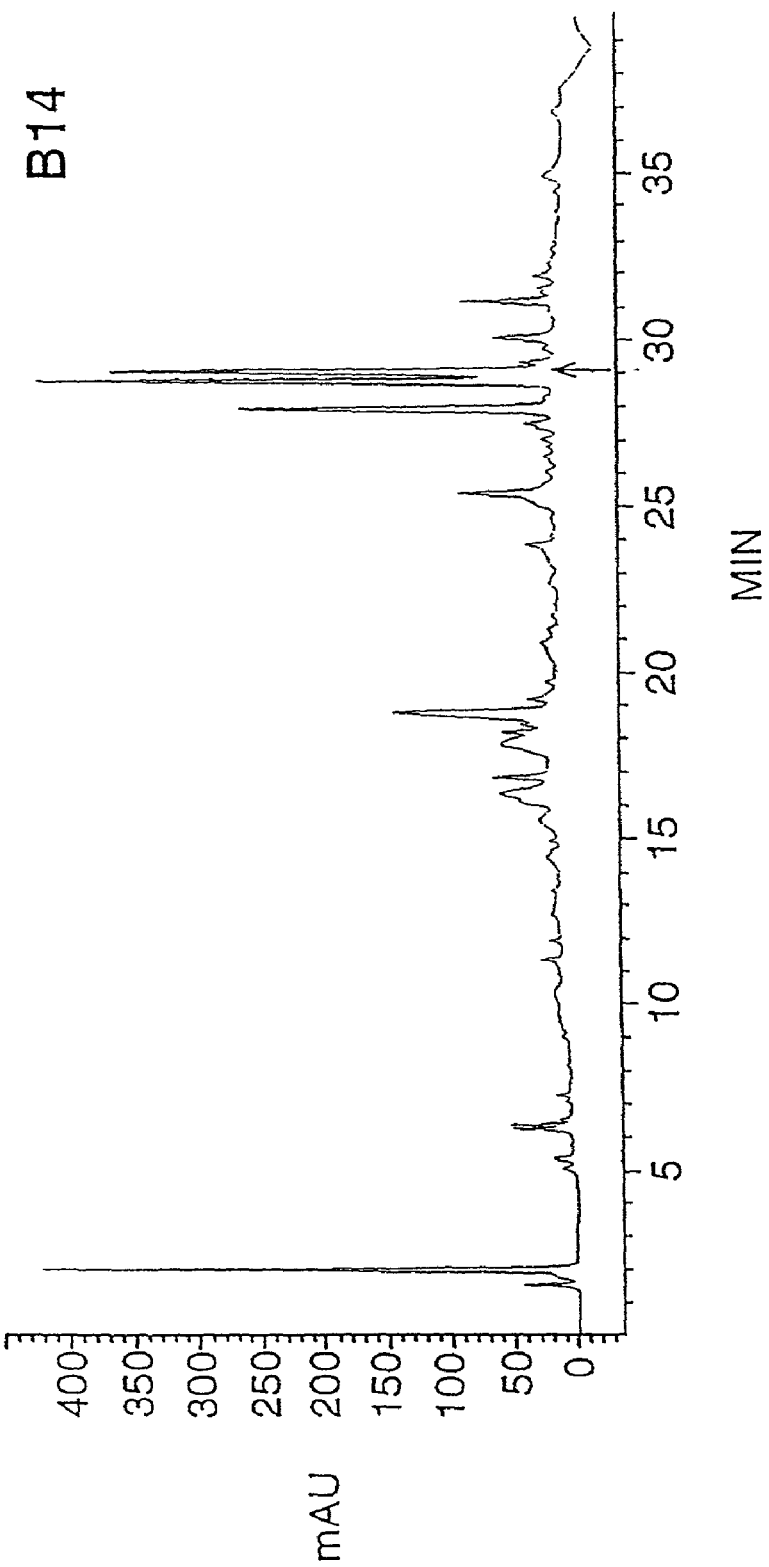
FIG. 8c is a chromatogram for a reference sample illustrated for comparison with the chromatograms of FIGS. 8a and 8b.

This is exemplified in FIG. 8a by the HPLC chromatogram for broth sample B19 which has a flatter baseline and shows better peak separation than the corresponding cell extract B14 illustrated in FIG. 8c. Where the replacement medium is water as in sample B16, the chromatogram is simplified even further (FIG. 8b).

TABLE 10

| Ref: | Organism | Metabolite | Inoculum Type | Growth Medium | Replacement Medium | Extract Type | Conc (mg/l) |
|---|---|---|---|---|---|---|---|
| | | | TEST | | | | |
| B1 | T. longibrachiatum 5602E | bisvertinolone | Layer | FS | water | cell | 0 |
| B2 | T. longibrachiatum 5602E | bisvertinolone | Layer | FS | glucidex | cell | 0 |
| B3 | T. longibrachiatum 5602E | bisvertinolone | Layer | FS | trehalose | cell | 43.6 |
| B4 | T. longibrachiatum 5602E | bisvertinolone | Layer | FS | glycerol | cell | 0 |
| B5 | T. longibrachiatum 5602E | bisvertinolone | Layer | FS | mannitol | cell | 0 |
| B6 | T. longibrachiatum 5602E | bisvertinolone | Layer | FS | water | broth | 406.3 |
| B7 | T. longibrachiatum 5602E | bisvertinolone | Layer | FS | glucidex | broth | 115.6 |
| B8 | T. longibrachiatum 5602E | bisvertinolone | Layer | FS | trehalose | broth | 196.0 |
| B9 | T. longibrachiatum 5602E | bisvertinolone | Layer | FS | glycerol | broth | 304.0 |
| B10 | T. longibrachiatum 5602E | bisvertinolone | Layer | FS | mannitol | broth | 168.3 |
| B11 | T. longibrachiatum 5602E | bisvertinolone | Layer | HC4 | water | cell | 0 |
| B12 | T. longibrachiatum 5602E | bisvertinolone | Layer | HC4 | glucidex | cell | 0 |
| B13 | T. longibrachiatum 5602E | bisvertinolone | Layer | HC4 | trehalose | cell | 322.6 |
| B14 | T. longibrachiatum 5602E | bisvertinolone | Layer | HC4 | glycerol | cell | 456.1 |
| B15 | T. longibrachiatum 5602E | bisvertinolone | Layer | HC4 | mannitol | cell | 240.2 |
| B16 | T. longibrachiatum 5602E | bisvertinolone | Layer | HC4 | water | broth | 798.3 |
| B17 | T. longibrachiatum 5602E | bisvertinolone | Layer | HC4 | glucidex | broth | 1448.0 |
| B18 | T. longibrachiatum 5602E | bisvertinolone | Layer | HC4 | trehalose | broth | 2505.0 |
| B19 | T. longibrachiatum 5602E | bisvertinolone | Layer | HC4 | glycerol | broth | 3407.9 |
| B20 | T. longibrachiatum 5602E | bisvertinolone | Layer | HC4 | mannitol | broth | 2326.1 |
| B21 | T. longibrachiatum 5602E | bisvertinolone | Plug | FS | water | cell | 0 |
| B22 | T. longibrachiatum 5602E | bisvertinolone | Plug | FS | glucidex | cell | 1669.9 |
| B23 | T. longibrachiatum 5602E | bisvertinolone | Plug | FS | trehalose | cell | 1325.2 |
| B24 | T. longibrachiatum 5602E | bisvertinolone | Plug | FS | glycerol | cell | 901.7 |
| B25 | T. longibrachiatum 5602E | bisvertinolone | Plug | FS | mannitol | cell | 1333.6 |
| B26 | T. longibrachiatum 5602E | bisvertinolone | Plug | FS | water | broth | 1214.6 |
| B27 | T. longibrachiatum 5602E | bisvertinolone | Plug | FS | glucidex | broth | 1439.8 |
| B28 | T. longibrachiatum 5602E | bisvertinolone | Plug | FS | trehalose | broth | 617.6 |
| B29 | T. longibrachiatum 5602E | bisvertinolone | Plug | FS | glycerol | broth | 802.2 |
| B30 | T. longibrachiatum 5602E | bisvertinolone | Plug | FS | mannitol | broth | 1227.8 |
| B31 | T. longibrachiatum 5602E | bisvertinolone | Plug | HC4 | water | cell | 432.9 |
| B32 | T. longibrachiatum 5602E | bisvertinolone | Plug | HC4 | glucidex | cell | 1046.2 |
| B33 | T. longibrachiatum 5602E | bisvertinolone | Plug | HC4 | trehalose | cell | 219.6 |
| B34 | T. longibrachiatum 5602E | bisvertinolone | Plug | HC4 | glycerol | cell | 276.6 |
| B35 | T. longibrachiatum 5602E | bisvertinolone | Plug | HC4 | mannitol | cell | 378.0 |
| B36 | T. longibrachiatum 5602E | bisvertinolone | Plug | HC4 | water | broth | 798.4 |
| B37 | T. longibrachiatum 5602E | bisvertinolone | Plug | HC4 | glucidex | broth | 2821.6 |
| B38 | T. longibrachiatum 5602E | bisvertinolone | Plug | HC4 | trehalose | broth | 1510.8 |
| B39 | T. longibrachiatum 5602E | bisvertinolone | Plug | HC4 | glycerol | broth | 3263.7 |
| B40 | T. longibrachiatum 5602E | bisvertinolone | Plug | HC4 | mannitol | broth | 2078.7 |
| | | | CONTROL | | | | |
| B41 | T. longibrachiatum 5602E | bisvertinolone | Layer | FS | FS | cell | 892.9 |
| B42 | T. longibrachiatum 5602E | bisvertinolone | Layer | FS | FS | broth | 344.7 |
| B43 | T. longibrachiatum 5602E | bisvertinolone | Layer | HC4 | HC4 | cell | 5256.5 |
| B44 | T. longibrachiatum 5602E | bisvertinolone | Layer | HC4 | HC4 | broth | 2451.2 |
| B45 | T. longibrachiatum 5602E | bisvertinolone | Plug | FS | FS | cell | 659.5 |
| B46 | T. longibrachiatum 5602E | bisvertinolone | Plug | FS | FS | broth | 660.5 |
| B47 | T. longibrachiatum 5602E | bisvertinolone | Plug | HC4 | HC4 | cell | 1470.4 |
| B48 | T. longibrachiatum 5602E | bisvertinolone | Plug | HC4 | HC4 | broth | 2186.5 |
| B49 | T. longibrachiatum 5602E | bisvertinolone | Shaken | FS | | culture | 6400 |

From the results, it can be observed that the fungus produces its secondary metabolite under most circumstances, generally as effectively in the apparatus of the present invention as in traditional shaken cultures.

The apparatus allows for secretion of secondary metabolites into the highly defined replacement medium and the generation of less complex mixtures of wholly fungal origin.

EXAMPLE C

Amycolatopsis orientalis C2726

This actinomycete bacterium produces vancomycin. The results of the procedures applied to the microorganism are set out in Table 11.

TABLE 11

| Ref: | Organism | Metabolite | Inoculum Type | Growth Medium | Replacement Medium | Extract Type | Conc. (mg/l) |
|---|---|---|---|---|---|---|---|
| | | | TEST | | | | |
| C1 | A orientalis C2726 | vancomycin | Layer | SV2 | water | cell | 0 |
| C2 | A orientalis C2726 | vancomycin | Layer | SV2 | glucidex | cell | 0 |
| C3 | A orientalis C2726 | vancomycin | Layer | SV2 | glucidex + proline | cell | 0 |
| C4 | A orientalis C2726 | vancomycin | Layer | SV2 | glycerol | cell | 0 |
| C5 | A orientalis C2726 | vancomycin | Layer | SV2 | glycerol + proline | cell | 0 |
| C6 | A orientalis C2726 | vancomycin | Layer | SV2 | water | broth | 52.1 |
| C7 | A orientalis C2726 | vancomycin | Layer | SV2 | glucidex | broth | 79.3 |
| C8 | A orientalis C2726 | vancomycin | Layer | SV2 | glucidex + proline | broth | 49.8 |
| C9 | A orientalis C2726 | vancomycin | Layer | SV2 | glycerol | broth | 76.9 |
| C10 | A orientalis C2726 | vancomycin | Layer | SV2 | glycerol + proline | broth | 58.6 |
| C11 | A orientalis C2726 | vancomycin | Layer | MPGS | water | cell | 0 |
| C12 | A orientalis C2726 | vancomycin | Layer | MPGS | glucidex | cell | 0 |
| C13 | A orientalis C2726 | vancomycin | Layer | MPGS | glucidex + proline | cell | 0 |
| C14 | A orientalis C2726 | vancomycin | Layer | MPGS | glycerol | cell | 0 |
| C15 | A orientalis C2726 | vancomycin | Layer | MPGS | glycerol + proline | cell | 0 |
| C16 | A orientalis C2726 | vancomycin | Layer | MPGS | water | broth | 20.3 |
| C17 | A orientalis C2726 | vancomycin | Layer | MPGS | glucidex | broth | 95.2 |
| C18 | A orientalis C2726 | vancomycin | Layer | MPGS | glucidex + proline | broth | 120.9 |
| C19 | A orientalis C2726 | vancomycin | Layer | MPGS | glycerol | broth | 142.3 |
| C20 | A orientalis C2726 | vancomycin | Layer | MPGS | glycerol + proline | broth | 207.9 |
| C21 | A orientalis C2726 | vancomycin | Plug | SV2 | water | cell | 0 |
| C22 | A orientalis C2726 | vancomycin | Plug | SV2 | glucidex | cell | 0 |
| C23 | A orientalis C2726 | vancomycin | Plug | SV2 | glucidex + proline | cell | 14.6 |
| C24 | A orientalis C2726 | vancomycin | Plug | SV2 | glycerol | cell | 6.6 |
| C25 | A orientalis C2726 | vancomycin | Plug | SV2 | glycerol + proline | cell | 36.9 |
| C26 | A orientalis C2726 | vancomycin | Plug | SV2 | water | broth | 15.1 |
| C27 | A orientalis C2726 | vancomycin | Plug | SV2 | glucidex | broth | 9.1 |
| C28 | A orientalis C2726 | vancomycin | Plug | SV2 | glucidex + proline | broth | 73.5 |
| C29 | A orientalis C2726 | vancomycin | Plug | SV2 | glycerol | broth | 110.8 |
| C30 | A orientalis C2726 | vancomycin | Plug | SV2 | glycerol + proline | broth | 86.9 |
| C31 | A orientalis C2726 | vancomycin | Plug | MPGS | water | cell | 00 |
| C32 | A orientalis C2726 | vancomycin | Plug | MPGS | glucidex | cell | 00 |
| C33 | A orientalis C2726 | vancomycin | Plug | MPGS | glucidex + proline | cell | 8.2 |
| C34 | A orientalis C2726 | vancomycin | Plug | MPGS | glycerol | cell | 6.8 |
| C35 | A orientalis C2726 | vancomycin | Plug | MPGS | glycerol + proline | cell | 15.1 |
| C36 | A orientalis C2726 | vancomycin | Plug | MPGS | water | broth | 00 |
| C37 | A orientalis C2726 | vancomycin | Plug | MPGS | glucidex | broth | 17.4 |
| C38 | A orientalis C2726 | vancomycin | Plug | MPGS | glucidex + proline | broth | 43.9 |
| C39 | A orientalis C2726 | vancomycin | Plug | MPGS | glycerol | broth | 51.1 |
| C40 | A orientalis C2726 | vancomycin | Plug | MPGS | glycerol + proline | broth | 36.1 |
| | | | CONTROL | | | | |
| C41 | A orientalis C2726 | vancomycin | Layer | SV2 | SV2 | cell | 29.3 |
| C42 | A orientalis C2726 | vancomycin | Layer | SV2 | SV2 | broth | 0 |
| C43 | A orientalis C2726 | vancomycin | Layer | MPGS | MPGS | cell | 0 |
| C44 | A orientalis C2726 | vancomycin | Layer | MPGS | MPGS | broth | 0 |
| C45 | A orientalis C2726 | vancomycin | Plug | SV2 | SV2 | cell | 0 |
| C46 | A orientalis C2726 | vancomycin | Plug | SV2 | SV2 | broth | 0 |
| C47 | A orientalis C2726 | vancomycin | Layer | MPGS | MPGS | cell | 0 |
| C48 | A orientalis C2726 | vancomycin | Layer | MPGS | MPGS | broth | 0 |
| C49 | A orientalis C2726 | vancomycin | Shaken | BFMS | | culture | 307 |

The results show that the apparatus supports the production of vancomycin by this actinomycete, specifically in the broth of layer cultures and more generally over plug cultures. The generally poorer performance of water as a replacement medium indicates the importance of a carbon source or a carbon and nitrogen source in a specified ratio, to enhance the production of vancomycin.

In the eight control cultures C41 to C48 performed in apparatus as describe-d above, vancomycin is only detectable in one culture C41. These results indicate that a nutrient replacement procedure to media containing a carbon or carbon and nitrogen source is essential to consistently produce vancomycin from the primary growth media SV2 and MPGS.

Figure 9C:
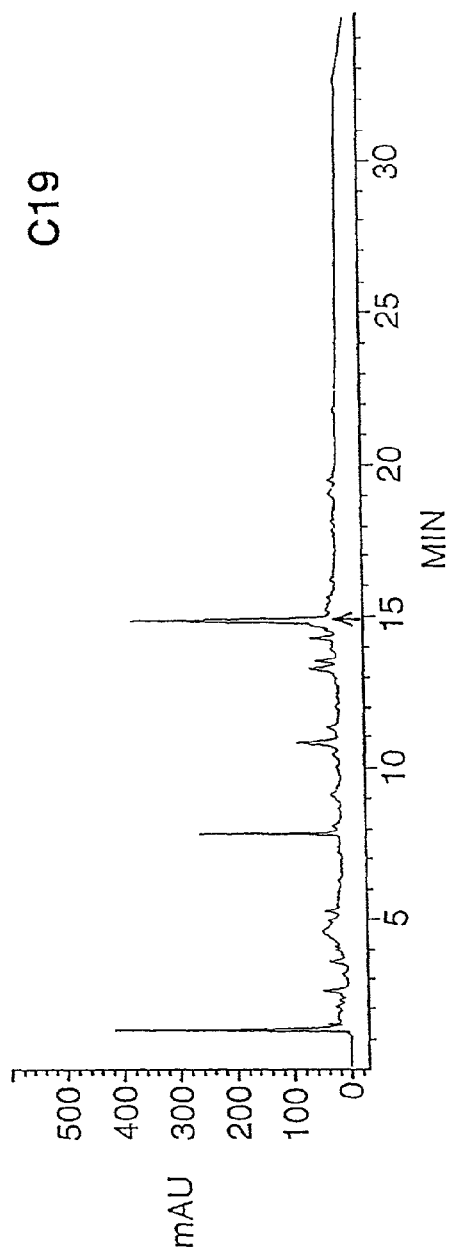
FIG. 9c is a chromatogram for a third test sample prepared in accordance with a third example of a specific method in accordance with the present invention.
Figure 9D:
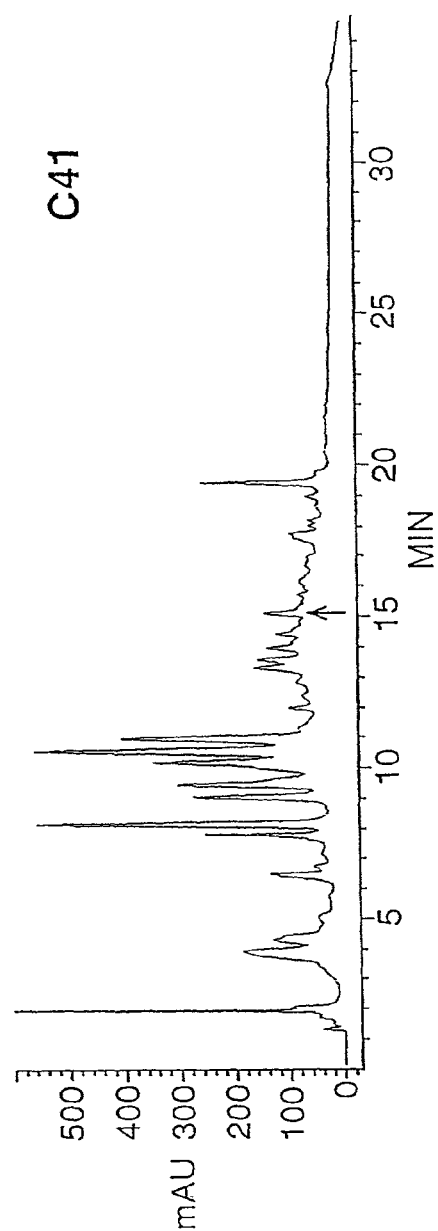
FIG. 9d is a chromatogram for a control sample illustrated for comparison with the chromatograms of FIGS. 9a, 9b, and 9c.

HPLC chromatograms for broths exemplified in FIGS. 9a, 9b and 9c, for samples C16, C17 and C19 respectively, show flatter baselines, fewer components and better peak separation than the control cell extract exemplified by sample C41, whose HPLC chromatogram is illustrated in FIG. 9d. In addition, comparison of the HPLC chromatograms for individual spectra exemplified by samples C16, C17 and C19 show differences in vancomycin titre and subtle differences in the overall pattern of peaks.

EXAMPLE D

*Nocardiopsis sp.* 5997E

This actinomycete bacterium produces K252a. The results of the procedures applied to the microorganism are set out in Table 12.

TABLE 12

| Ref. | Organism | Metabolite | Inoculum Type | Growth Medium | Replacement Medium | Extract Type | Conc. (mg/l) |
|---|---|---|---|---|---|---|---|
| TEST | | | | | | | |
| D1 | Nocardiopsis sp 5997E | K252a | Layer | SV2 | water | cell | 15 |
| D2 | Nocardiopsis sp 5997E | K252a | Layer | SV2 | glucidex | cell | 0 |
| D3 | Nocardiopsis sp 5997E | K252a | Layer | SV2 | glucidex + proline | cell | 13 |
| D4 | Nocardiopsis sp 5997E | K252a | Layer | SV2 | glycerol | cell | 46 |
| D5 | Nocardiopsis sp 5997E | K252a | Layer | SV2 | glycerol + proline | cell | 32 |
| D6 | Nocardiopsis sp 5997E | K252a | Layer | SV2 | water | broth | 0 |
| D7 | Nocardiopsis sp 5997E | K252a | Layer | SV2 | glucidex | broth | 0 |
| D8 | Nocardiopsis sp 5997E | K252a | Layer | SV2 | glucidex + proline | broth | 0 |
| D9 | Nocardiopsis sp 5997E | K252a | Layer | SV2 | glycerol | broth | 0 |
| D10 | Nocardiopsis sp 5997E | K252a | Layer | SV2 | glycerol + proline | broth | 0 |
| D11 | Nocardiopsis sp 5997E | K252a | Layer | MPGS | water | cell | 1962 |
| D12 | Nocardiopsis sp 5997E | K252a | Layer | MPGS | glucidex | cell | 1991 |
| D13 | Nocardiopsis sp 5997E | K252a | Layer | MPGS | glucidex + proline | cell | 2342 |
| D14 | Nocardiopsis sp 5997E | K252a | Layer | MPGS | glycerol | cell | 2275 |
| D15 | Nocardiopsis sp 5997E | K252a | Layer | MPGS | glycerol + proline | cell | 2435 |
| D16 | Nocardiopsis sp 5997E | K252a | Layer | MPGS | water | broth | 0 |
| D17 | Nocardiopsis sp 5997E | K252a | Layer | MPGS | glucidex | broth | 0 |
| D18 | Nocardiopsis sp 5997E | K252a | Layer | MPGS | glucidex + proline | broth | 0 |
| D19 | Nocardiopsis sp 5997E | K252a | Layer | MPGS | glycerol | broth | 0 |
| D20 | Nocardiopsis sp 5997E | K252a | Layer | MPGS | glycerol + proline | broth | 0 |
| D21 | Nocardiopsis sp 5997E | K252a | Plug | SV2 | water | cell | 0 |
| D22 | Nocardiopsis sp 5997E | K252a | Plug | SV2 | glucidex | cell | 0 |
| D23 | Nocardiopsis sp 5997E | K252a | Plug | SV2 | glucidex + proline | cell | 0 |
| D24 | Nocardiopsis sp 5997E | K252a | Plug | SV2 | glycerol | cell | 0 |
| D25 | Nocardiopsis sp 5997E | K252a | Plug | SV2 | glycerol + proline | cell | 0 |
| D26 | Nocardiopsis sp 5997E | K252a | Plug | SV2 | water | broth | 0 |
| D27 | Nocardiopsis sp 5997E | K252a | Plug | SV2 | glucidex | broth | 0 |
| D28 | Nocardiopsis sp 5997E | K252a | Plug | SV2 | glucidex + proline | broth | 0 |
| D29 | Nocardiopsis sp 5997E | K252a | Plug | SV2 | glycerol | broth | 0 |
| D30 | Nocardiopsis sp 5997E | K252a | Plug | SV2 | glycerol + proline | broth | 0 |
| D31 | Nocardiopsis sp 5997E | K252a | Plug | MPGS | water | cell | 0 |
| D32 | Nocardiopsis sp 5997E | K252a | Plug | MPGS | glucidex | cell | 0 |
| D33 | Nocardiopsis sp 5997E | K252a | Plug | MPGS | glucidex + proline | cell | 0 |
| D34 | Nocardiopsis sp 5997E | K252a | Plug | MPGS | glycerol | cell | 0 |
| D35 | Nocardiopsis sp 5997E | K252a | Plug | MPGS | glycerol + proline | cell | 0 |
| D36 | Nocardiopsis sp 5997E | K252a | Plug | MPGS | water | broth | 0 |
| D37 | Nocardiopsis sp 5997E | K252a | Plug | MPGS | glucidex | broth | 0 |
| D38 | Nocardiopsis sp 5997E | K252a | Plug | MPGS | glucidex + proline | broth | 0 |
| D39 | Nocardiopsis sp 5997E | K252a | Plug | MPGS | glycerol | broth | 0 |
| D40 | Nocardiopsis sp 5997E | K252a | Plug | MPGS | glycerol + proline | broth | 0 |
| CONTROL | | | | | | | |
| D41 | Nocardiopsis sp 5997E | K252a | Layer | SV2 | SV2 | cell | 0 |
| D42 | Nocardiopsis sp 5997E | K252a | Layer | SV2 | SV2 | broth | 0 |
| D43 | Nocardiopsis sp 5997E | K252a | Layer | MPGS | MPGS | cell | 2284 |
| D44 | Nocardiopsis sp 5997E | K252a | Layer | MPGS | MPGS | broth | 644 |
| D45 | Nocardiopsis sp 5997E | K252a | Plug | SV2 | SV2 | cell | 0 |
| D46 | Nocardiopsis sp 5997E | K252a | Plug | SV2 | SV2 | broth | 0 |
| D47 | Nocardiopsis sp 5997E | K252a | Plug | MPGS | MPGS | cell | 0 |
| D48 | Nocardiopsis sp 5997E | K252a | Plug | MPGS | MPGS | broth | 0 |
| D49 | Nocardiopsis sp 5997E | K252a | Shaken | K252/P1 | | culture | 2108 |

Figure 10A:
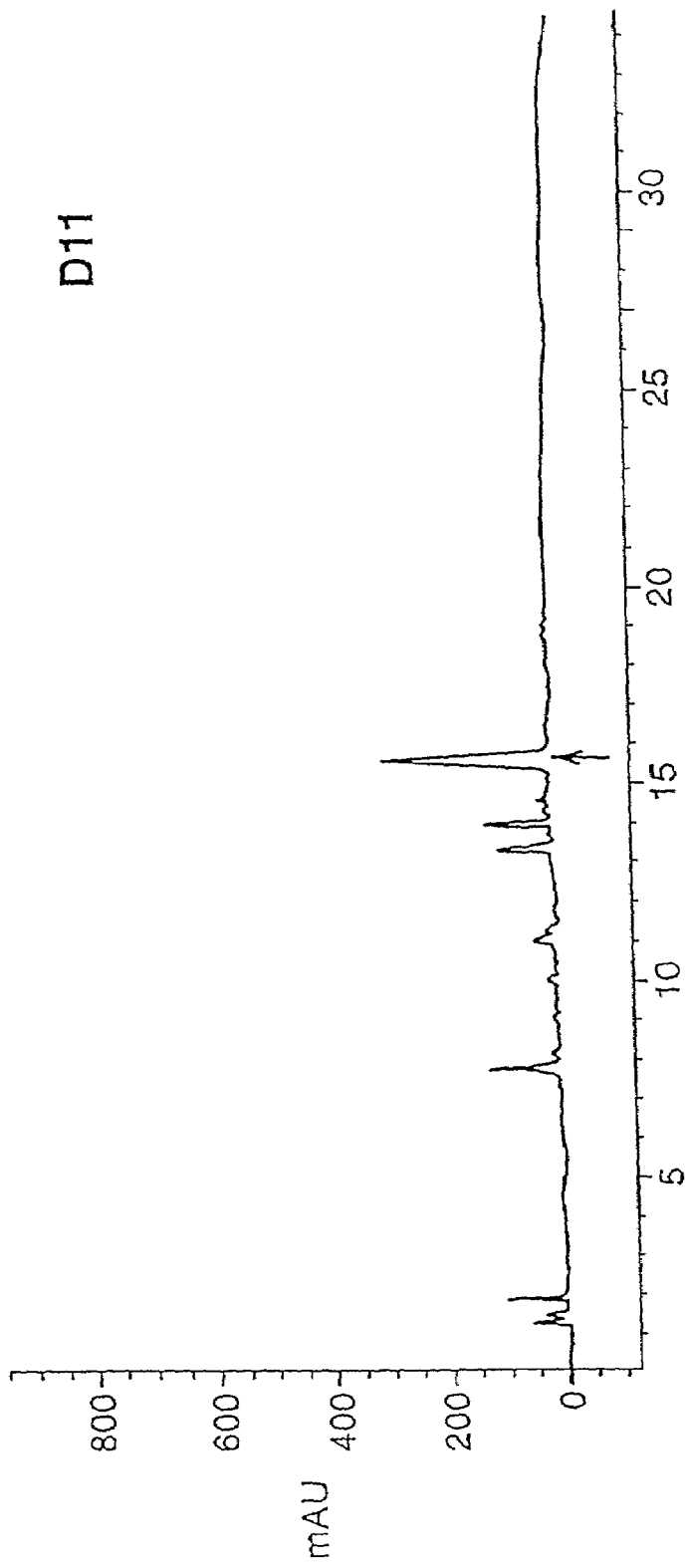
FIG. 10a is a chromatogram for a first test sample prepared in accordance with a fourth example of a specific method in accordance with the present invention.
Figure 10B:
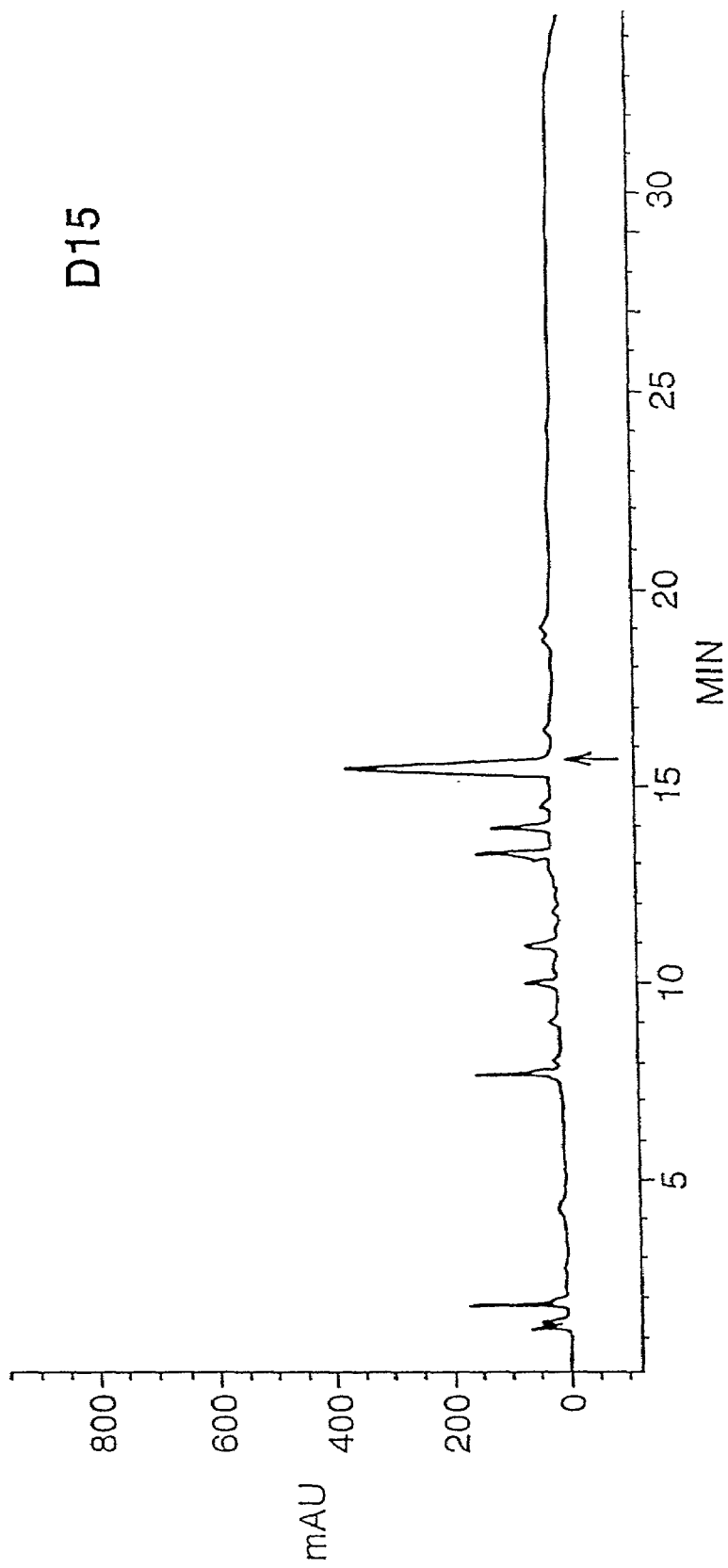
FIG. 10b is a chromatogram for a second test sample prepared in accordance with a fourth example of a specific method in accordance with the present invention.
Figure 10C:
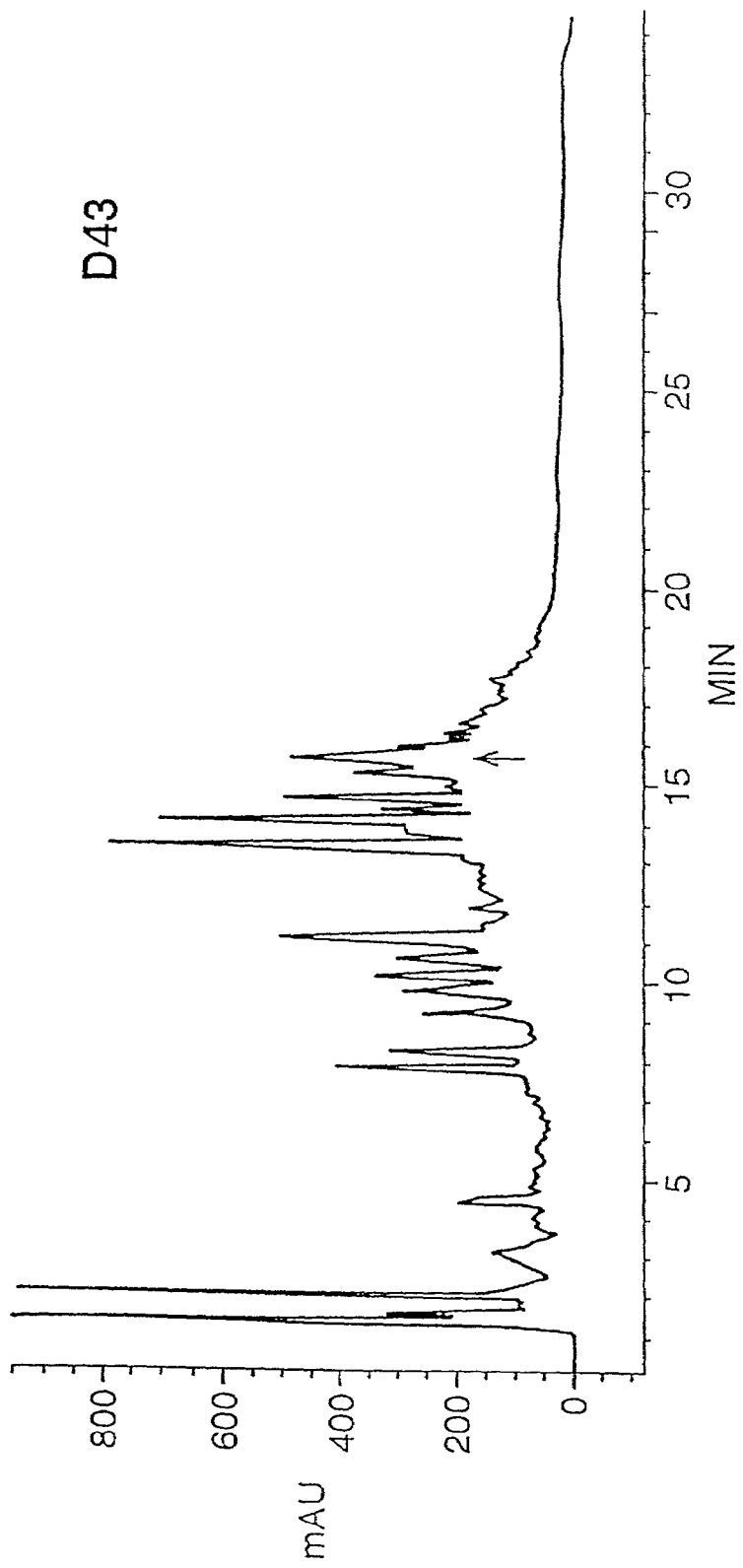
FIG. 10c is a chromatogram for a control sample illustrated for comparison with the chromatograms of FIGS. 10a and 10b.

The results show that metabolite K252a is most effectively produced in cell extracts of layer cultures transferred to replacement medium following growth in MPGS medium. Titres of K252a in these culture samples D11 to D15 are not significantly different from the control culture D43. However, comparison of HPLC spectra for samples D11 and D15, as illustrated in FIGS. 10a and 10b, show that cell extracts for those samples contain fewer, well defined peaks than shown in the HPLC chromatogram for control sample D43 (FIG. 10c), indicating the existence of simpler solutions.

Again this example shows that although the titres are low, the described procedure induces production of K252a in SV2 medium when none is produced under control conditions. This demonstrates that the apparata can be used to produce secondary metabolites through the use of only a limited number of media, whereas up to ten media would previously have been required.

EXAMPLE E

*Streptomyces citricolor* C2778

This actinomycete bacterium produces the compound aristeromycin. The results of the procedures applied to the microorganism are set out in Table 13.

TABLE 13

| Ref: | Organism | Metabolite | Inoculum Type | Growth Medium | Replacement Medium | Extract Type | Conc. (mg/l) |
|---|---|---|---|---|---|---|---|
| | | | TEST | | | | |
| E1 | S. citricolor C2778 | ansteromycin | Layer | SV2 | water | cell | 5 |
| E2 | S. citricolor C2778 | ansteromycin | Layer | SV2 | glucidex | cell | 3 |
| E3 | S. citricolor C2778 | ansteromycin | Layer | SV2 | glucidex + proline | cell | 9 |
| E4 | S. citricolor C2778 | ansteromycin | Layer | SV2 | glycerol | cell | 3 |
| E5 | S. citricolor C2778 | ansteromycin | Layer | SV2 | glycerol + proline | cell | 10 |
| E6 | S. citricolor C2778 | ansteromycin | Layer | SV2 | water | broth | 22 |
| E7 | S. citricolor C2778 | ansteromycin | Layer | SV2 | glucidex | broth | 20 |
| E8 | S. citricolor C2778 | ansteromycin | Layer | SV2 | glucidex + proline | broth | 28 |
| E9 | S. citricolor C2778 | ansteromycin | Layer | SV2 | glycerol | broth | 16 |
| E10 | S. citricolor C2778 | ansteromycin | Layer | SV2 | glycerol + proline | broth | 41 |
| E11 | S. citricolor C2778 | ansteromycin | Layer | MPGS | water | cell | 3 |
| E12 | S. citricolor C2778 | ansteromycin | Layer | MPGS | glucidex | cell | 9 |
| E13 | S. citricolor C2778 | ansteromycin | Layer | MPGS | glucidex + proline | cell | 16 |
| E14 | S. citricolor C2778 | ansteromycin | Layer | MPGS | glycerol | cell | 12 |
| E15 | S. citricolor C2778 | ansteromycin | Layer | MPGS | glycerol + proline | cell | 5 |
| E16 | S. citricolor C2778 | ansteromycin | Layer | MPGS | water | broth | 23 |
| E17 | S. citricolor C2778 | ansteromycin | Layer | MPGS | glucidex | broth | 36 |
| E18 | S. citricolor C2778 | ansteromycin | Layer | MPGS | glucidex + proline | broth | 48 |
| E19 | S. citricolor C2778 | ansteromycin | Layer | MPGS | glycerol | broth | 68 |
| E20 | S. citricolor C2778 | ansteromycin | Layer | MPGS | glycerol + proline | broth | 37 |
| E21 | S. citricolor C2778 | ansteromycin | Plug | SV2 | water | cell | 0 |
| E22 | S. citricolor C2778 | ansteromycin | Plug | SV2 | glucidex | cell | 0 |
| E23 | S. citricolor C2778 | ansteromycin | Plug | SV2 | glucidex + proline | cell | 0 |
| E24 | S. citricolor C2778 | ansteromycin | Plug | SV2 | glycerol | cell | 0 |
| E25 | S. citricolor C2778 | ansteromycin | Plug | SV2 | glycerol + proline | cell | 0 |
| E26 | S. citricolor C2778 | ansteromycin | Plug | SV2 | water | broth | 0 |
| E27 | S. citricolor C2778 | ansteromycin | Plug | SV2 | glucidex | broth | 0 |
| E28 | S. citricolor C2778 | ansteromycin | Plug | SV2 | glucidex + proline | broth | 0 |
| E29 | S. citricolor C2778 | ansteromycin | Plug | SV2 | glycerol | broth | 0 |
| E30 | S. citricolor C2778 | ansteromycin | Plug | SV2 | glycerol + proline | broth | 0 |
| E31 | S. citricolor C2778 | ansteromycin | Plug | MPGS | water | cell | 0 |
| E32 | S. citricolor C2778 | ansteromycin | Plug | MPGS | glucidex | cell | 0 |
| E33 | S. citricolor C2778 | ansteromycin | Plug | MPGS | glucidex + proline | cell | 0 |
| E34 | S. citricolor C2778 | ansteromycin | Plug | MPGS | glycerol | cell | 6 |
| E35 | S. citricolor C2778 | ansteromycin | Plug | MPGS | glycerol + proline | cell | 0 |
| E36 | S. citricolor C2778 | ansteromycin | Plug | MPGS | water | broth | 4 |
| E37 | S. citricolor C2778 | ansteromycin | Plug | MPGS | glucidex | broth | 2 |
| E38 | S. citricolor C2778 | ansteromycin | Plug | MPGS | glucidex + proline | broth | 0 |
| E39 | S. citricolor C2778 | ansteromycin | Plug | MPGS | glycerol | broth | 16 |
| E40 | S. citricolor C2778 | ansteromycin | Plug | MPGS | glycerol + proline | broth | 0 |
| | | | CONTROL | | | | |
| E41 | S. citricolor C2778 | ansteromycin | Layer | SV2 | SV2 | cell | 52 |
| E42 | S. citricolor C2778 | ansteromycin | Layer | SV2 | SV2 | broth | 1 |
| E43 | S. citricolor C2778 | ansteromycin | Layer | MPGS | MPGS | cell | 40 |
| E44 | S. citricolor C2778 | ansteromycin | Layer | MPGS | MPGS | broth | 51 |
| E45 | S. citricolor C2778 | ansteromycin | Plug | SV2 | SV2 | cell | 0 |
| E46 | S. citricolor C2778 | ansteromycin | Plug | SV2 | SV2 | broth | 0 |
| E47 | S. citricolor C2778 | ansteromycin | Plug | MPGS | MPGS | cell | 0 |
| E48 | S. citricolor C2778 | ansteromycin | Plug | MPGS | MPGS | broth | 0 |
| E49 | S. citricolor C2778 | ansteromycin | Shaken | GAM6 6 | | culture | 21 |

Figure 11A:
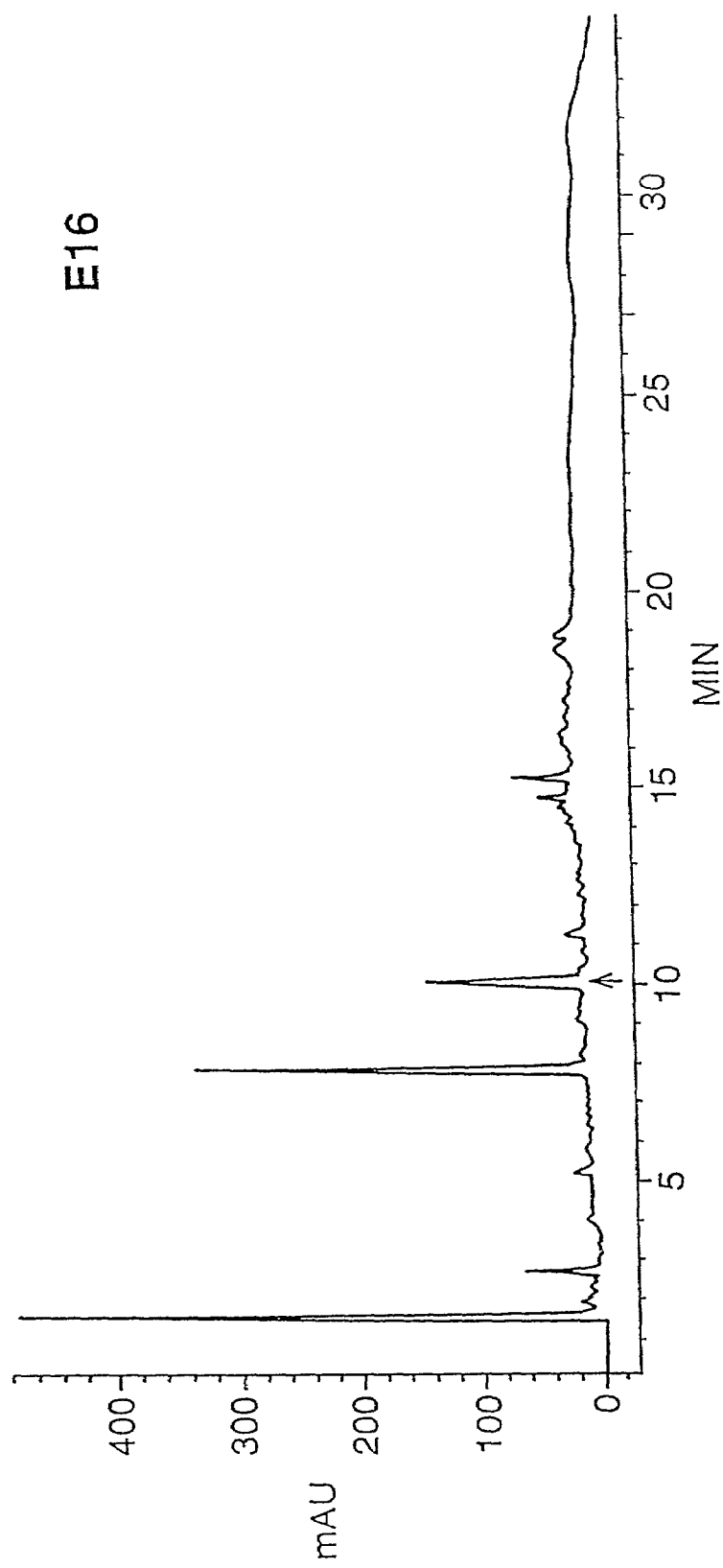
FIG. 11a is a chromatogram for a first test sample prepared in accordance with a fifth example of a specific method in accordance with the present invention.
Figure 11B:
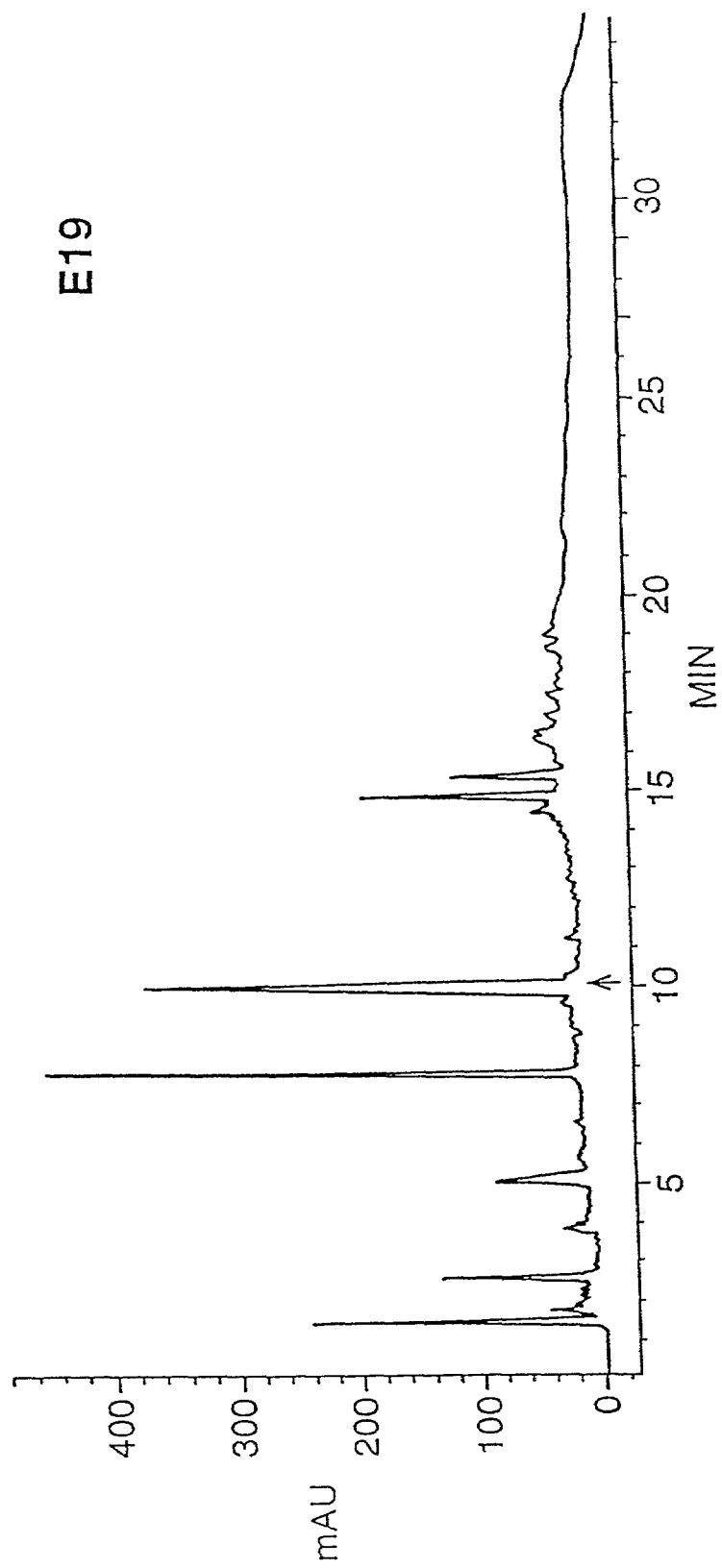
FIG. 11b is a chromatogram for a second test sample prepared in accordance with a fifth example of a specific method in accordance with the present invention.
Figure 11C:
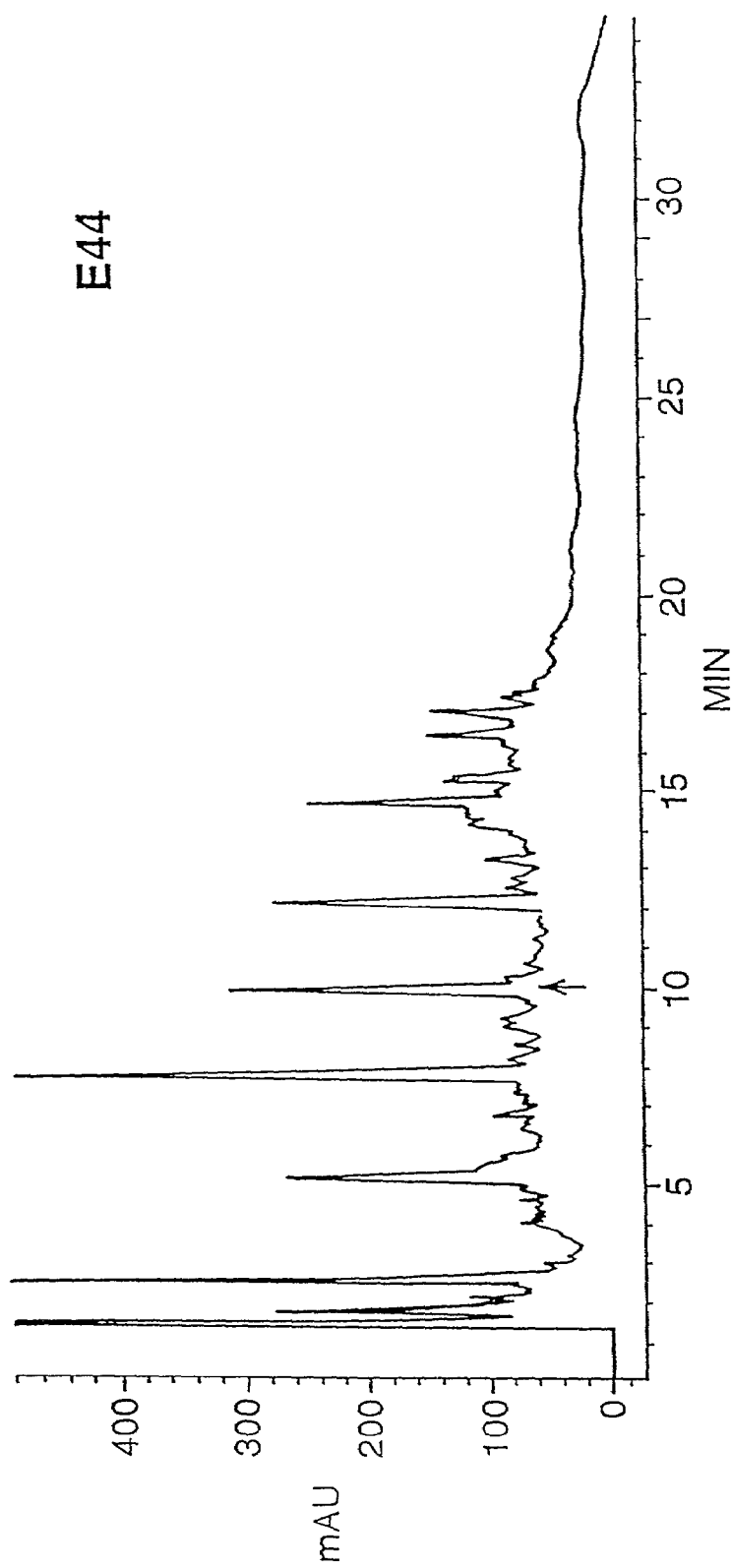
FIG. 11c is a chromatogram for a control sample illustrated for comparison with the chromatograms of FIGS. 11a and 11b.

The results show that the apparatus supports the production of aristeromycin by this actinomycete, specifically in layer cultures and more generally over plug cultures. In layer cultures and for both SV2 and MPGS media significantly higher levels of aristeromycin are found in the broth samples from cultures produced in accordance with the invention. The titres of aristeromycin in those cultures are comparable to the controls (no transfer to replacement medium) but HPLC chromatograms reveal that broth samples in those cultures are much simpler chemically than samples from the controls and contain a very much higher proportion of aristeromycin relative to other sample components. This is illustrated in FIGS. 11a and 11b with reference to E16 and E19, with their corresponding control sample E44 illustrated in FIG. 11c.

The examples set out above demonstrate that metabolite titres achieved in the apparatus of the specific embodiments of the invention approach those which are achievable in a traditional liquid shaken culture system which would use an optimised medium for a specific microorganism. The present invention as exemplified by the preceding procedures makes use of generalised growth media and replacement media which are nutrient deficient, rather than specialised media. By using generalised media, large scale trials with a plurality of different microorganisms can be made much more cost effective.

In all the examples where the secondary metabolite is secreted into the nutrient deficient medium, the proportion of metabolite relative to the other components, as indicated by HPLC, is very significantly enhanced over controls. This enables the sample to be concentrated by solvent evaporation to further increase the concentration of the specific metabolite without raising the concentration of non-specific components to a level where they would cause interference if the sample is tested in a biological assay. This equally applies to analysis by Matrix Assisted Laser Desorption Ionisation Time of Flight (MALDI-TOF) mass spectrometry (and other analytical systems) where the measurement of a desired analyte can be significantly enhanced by the removal of potentially interfering substances.

The enhanced resolution of peaks in HPLC chromatograms of samples as shown in FIGS. 7a, 8a and 8b, 9a, 9b and 9c, 10a and 10b, and 11a and 11b in comparison with FIGS. 7, 8c, 9d, 10c and 11c respectively demonstrates that the present method as exemplified herein permits easier separation of desired secondary metabolites from other chemicals than possible with previous fermentation apparatus and methods.

The invention allows for separation of the microorganism under investigation from the growth medium in which mycelial biomass is generated, in such a manner that secondary metabolism of the microorganism can be carefully controlled. Secondary metabolism can be carried out in a medium which is designed to promote production of a particular metabolite. In that way, specific components may be included in the replacement medium, as an inducer or precursor to the mechanism by which metabolites are produced. For example, test sample A25 demonstrates that mannitol has a stimulatory effect on the production of GR 195359 as a secondary metabolite of *Phoma sp.* F16006.

Further specific embodiments of the apparatus in accordance with the present invention will now be described with reference to FIGS. 12 to 18 of the accompanying drawings. It will be understood that the apparatus described below makes use of the same principles as the apparatus previously described, and so it can be used to generate secondary metabolites in the same manner. However, the apparatus described below has specific advantages which will become apparent from the following description.

Figure 12:
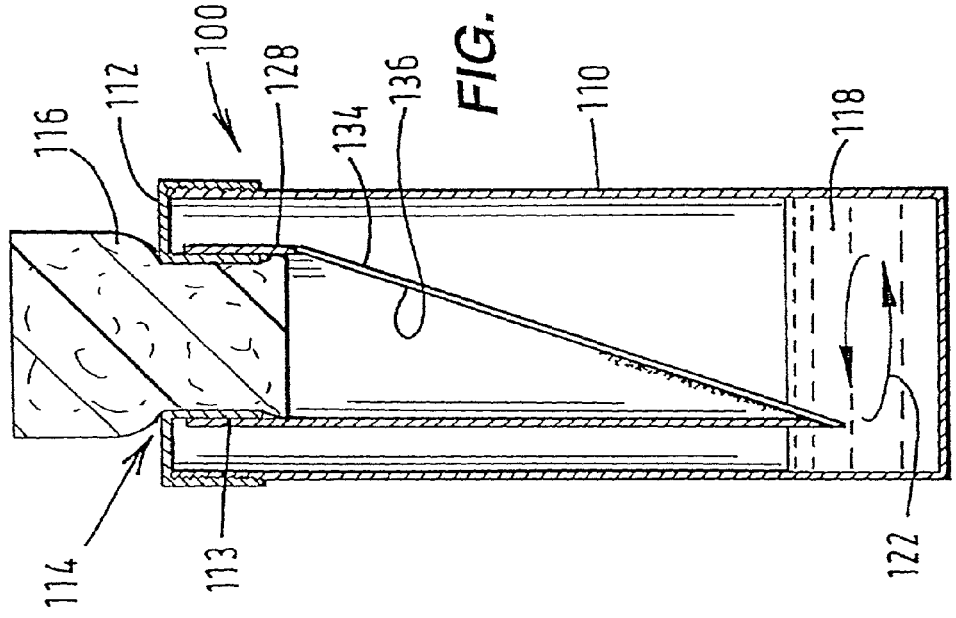
FIG. 12 is a schematic cross-sectional diagram of fermentation apparatus in accordance with a fourth specific embodiment of the invention.

With reference to FIG. 12, fermentation apparatus 100 in accordance with a fourth embodiment of the invention comprises a fermentation receptacle 110 of generally cylindrical shape. A lid 112 is threadingly engaged to one end thereof. The lid 112 has a throughbore 114, from which a peripheral flange 113 extends into the receptacle 110. A fermentation vessel 128 of generally cylindrical shape has an end taper-fitted to the flange 113. The opposite end of the vessel 128 is terminated at an acute angle to the longitudinal axis of the vessel 128, thereby forming a surface of elliptical shape. That end of the vessel 128 has two membranes 134, 136 formed thereacross, each being of 0.6 micrometers pore size hydrophilised melt cast polypropylene. The outer membrane 134 is fixed to the body of the vessel 128, and the inner membrane 136 is laid across the outer membrane 134. In that way, the inner membrane 136 can be removed from the vessel 128. A polystyrene foam filter 116 is placed in the bore 114.

By fitting the vessel 128 to the lid 112, the vessel 128 can be transferred into and out of the receptacle easily while maintaining aseptic conditions.

Figure 13:
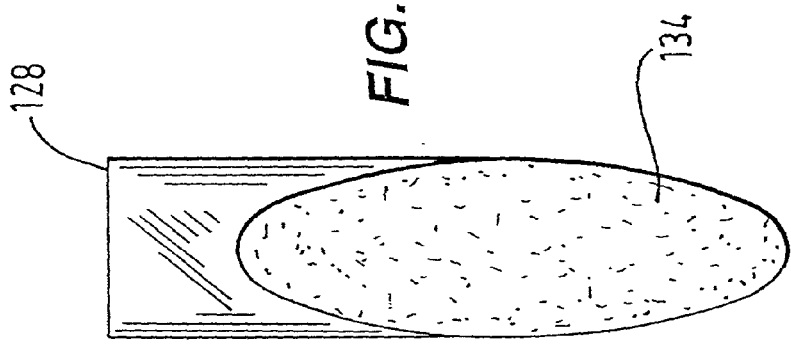
FIG. 13 is a side elevation of a fermentation vessel of the fermentation apparatus illustrated in FIG. 12.

FIG. 13 illustrates the fermentation vessel 128 in more detail. This shows the elliptical shape of the bottom end of the vessel 128, comprising the membrane 134.

The apparatus illustrated in FIG. 12 can be used to generate mycelial biomass, by including a quantity of a growth medium 118 in the receptacle 110. The tip of the vessel 128 dips into the growth medium, and the two membranes 134, 136 act as a wick, growth medium being drawn up into the membranes 134, 136 by capillary action. The inner membrane 136 is inoculated with a microorganism, which grows at the air/growth medium interface provided by the wicking membranes.

Figure 14:
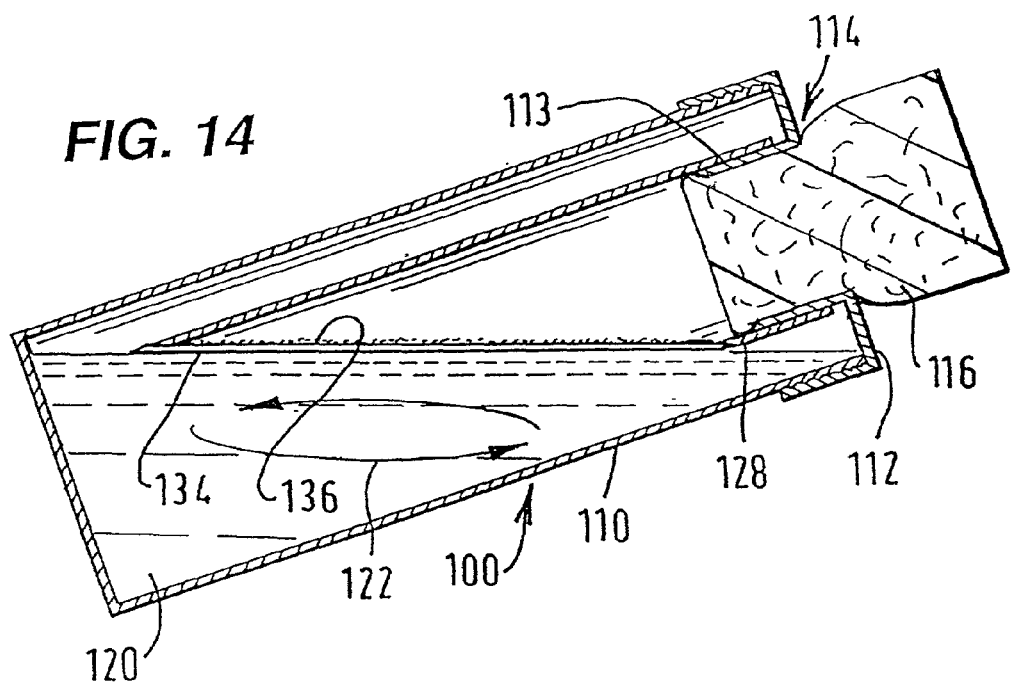
FIG. 14 is a schematic cross-sectional diagram of the fermentation apparatus illustrated in FIG. 12, in a mode of use operative to generate secondary metabolites.

FIG. 14 illustrates further use of the apparatus illustrated in FIG. 12. In this arrangement, the apparatus is shown after the growth medium 118 has been replaced by a replacement medium 120, deficient in particular nutrients so as to stimulate secondary metabolism. In this case, the apparatus 100 is tilted such that the replacement medium 120 makes contact with the entire outer membrane 134. Again, the inner and outer membranes 134, 136 act as wicks, but it is advantageous to have as much of the area of the membranes in contact with the liquid as possible, so as to promote secretion of secondary metabolites into the medium 120.

In both FIGS. 12 and 14, the apparatus can be agitated either by shaking or stirring as indicated by arrows 122, to promote aeration of the medium 118, 120.

Figure 15:
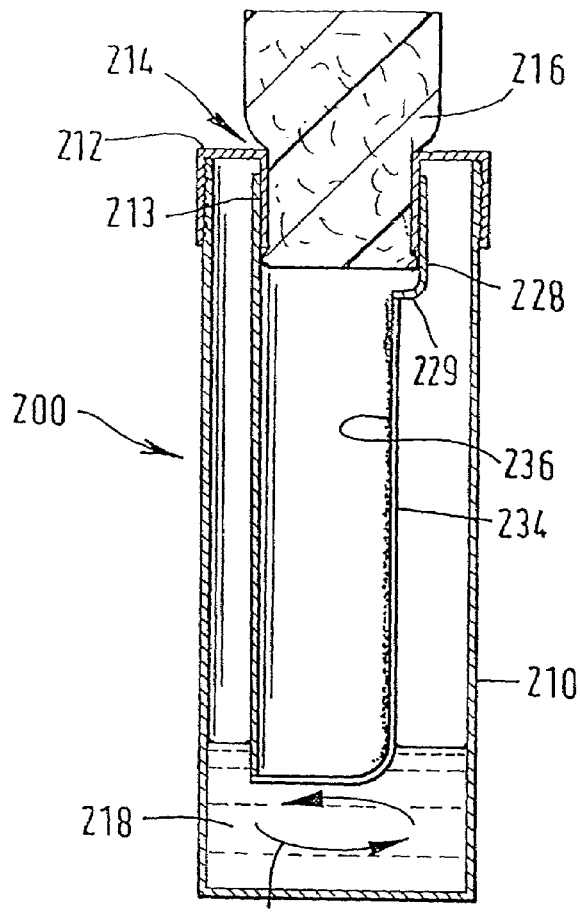
FIG. 15 is a schematic cross-sectional diagram of the fermentation apparatus in accordance with a fifth specific embodiment of the invention.

FIG. 15 shows a fifth specific embodiment of the apparatus in accordance with the invention. The apparatus 200 is of similar construction to the apparatus illustrated in FIG. 12. To the extent that the apparatus 200 includes a receptacle 210, a lid 212 with associated bore 214 and flange 213, and a foam plug 216, as described with reference to FIG. 12, no further description of those parts is necessary. However, the apparatus further includes a fermentation vessel 228 of different construction to the fermentation vessel illustrated in FIG. 12. In this case, the vessel 228 is formed with an outer membrane 234 extended substantially down the entire length of the vessel 228 except for a short length at which the vessel is taper-fitted to the flange 213. Furthermore, the outer membrane 234 extends over the opposite end of the vessel 228, which is illustrated dipped in a quantity of a growth medium 218. This provides a large area of membrane for growth of microorganism thereover. As in FIG. 12, the outer membrane 234 has an inner membrane 236 laid thereover, on which microorganism can be grown. At the end of the membrane 234 adjacent the portion of the vessel 228 to be taper fitted, the vessel 228 is provided with a radially inwardly extending dam 229.

Figure 16:
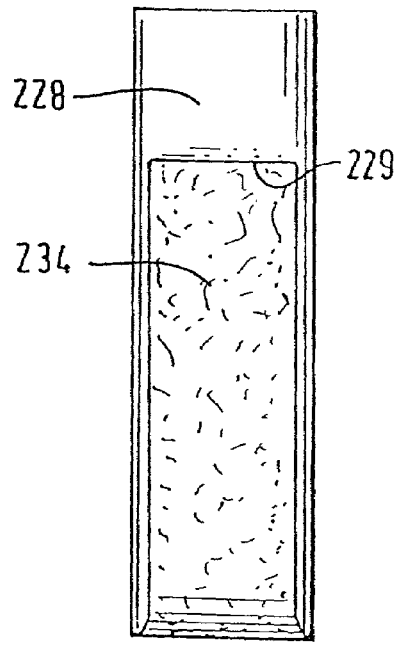
FIG. 16 is a side elevation of a fermentation vessel of the fermentation apparatus illustrated in FIG. 15.
Figure 17:
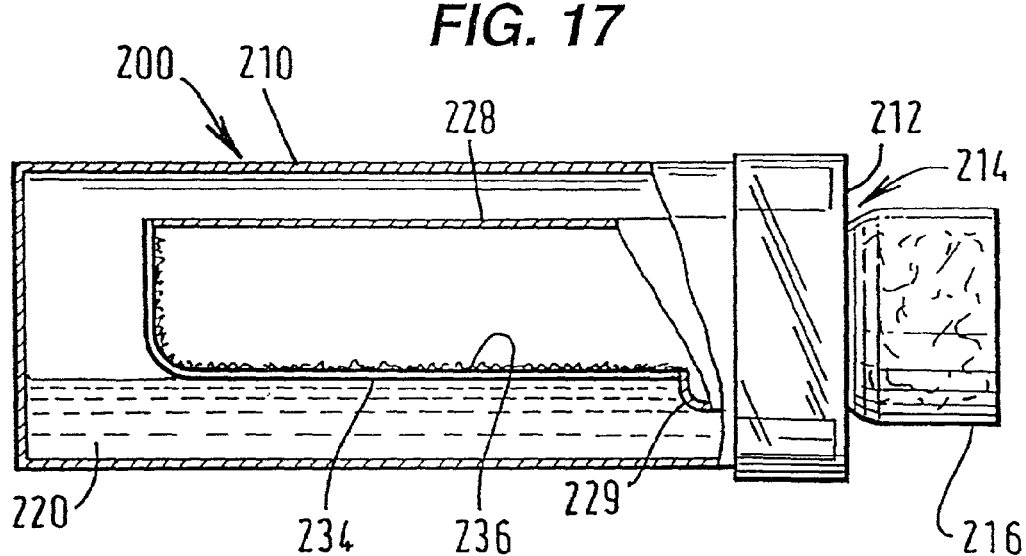
FIG. 17 is a schematic cross-sectional diagram of the fermentation apparatus illustrated in FIG. 15 in a mode of use operative to generate secondary metabolites.
Figure 18:
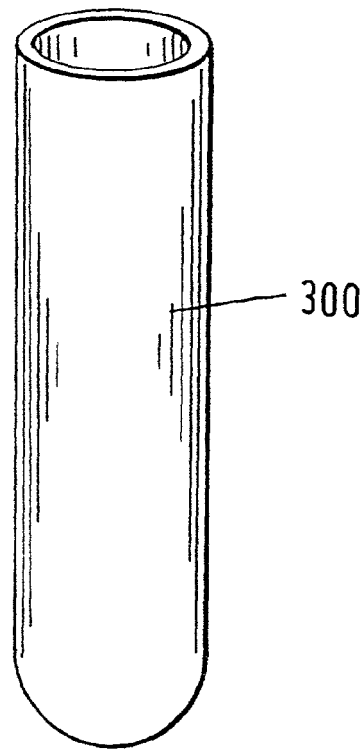
FIG. 18 is a perspective view of a fermentation vessel of fermentation apparatus in accordance with a sixth specific embodiment of the invention.
Figure 20:
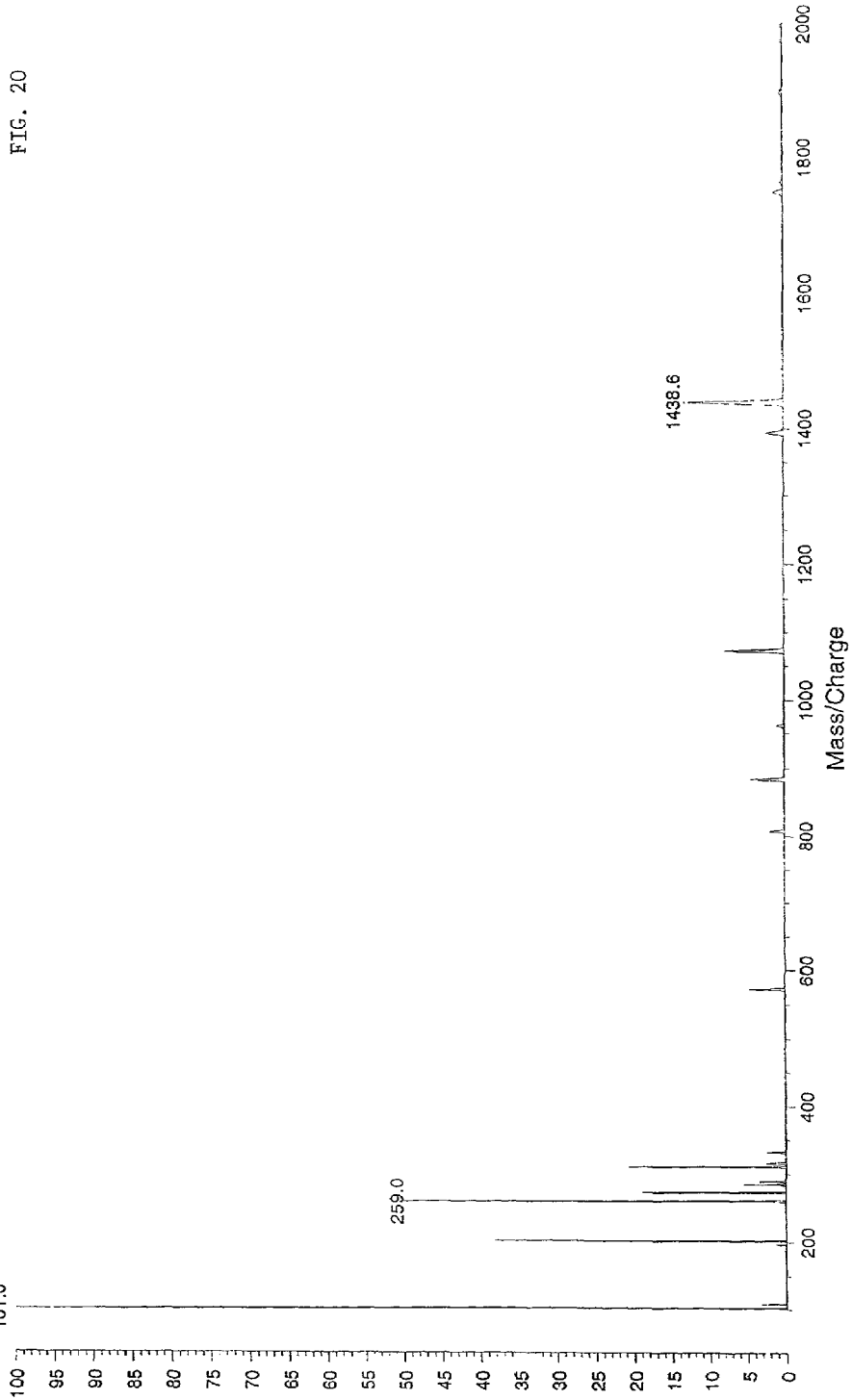
FIG. 20 is a spectrum generated by mass spectrometry of a control sample corresponding with the sample generated in the sixth example.
Figure 21A:
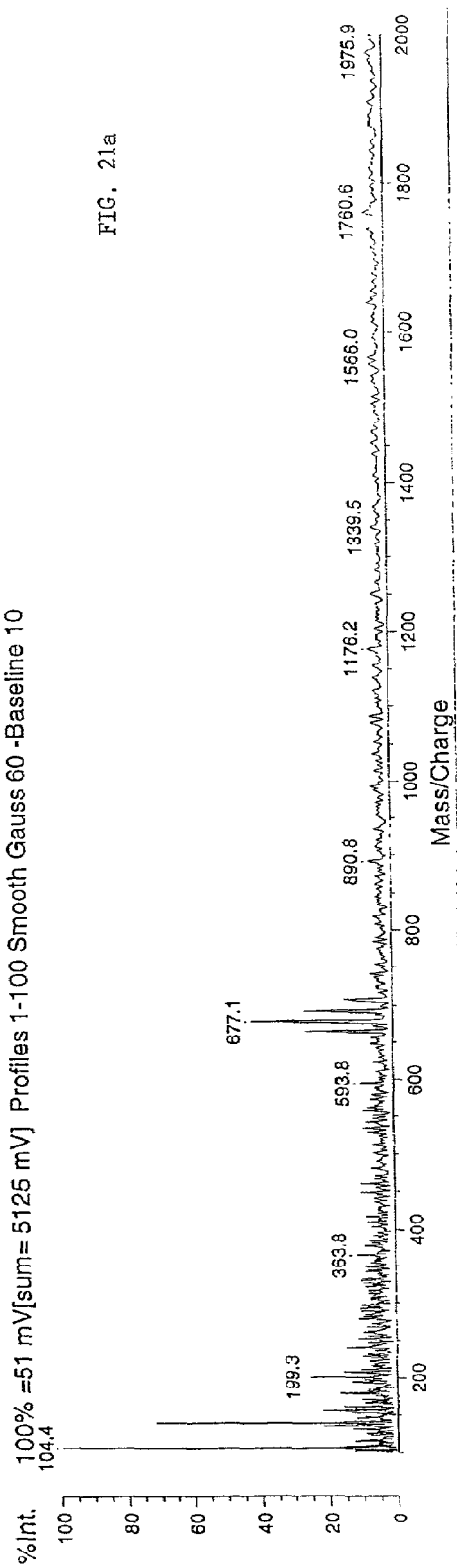
FIG. 21a is a spectrum generated by mass spectrometry of a further sample generated in the sixth example.
Figure 21B:
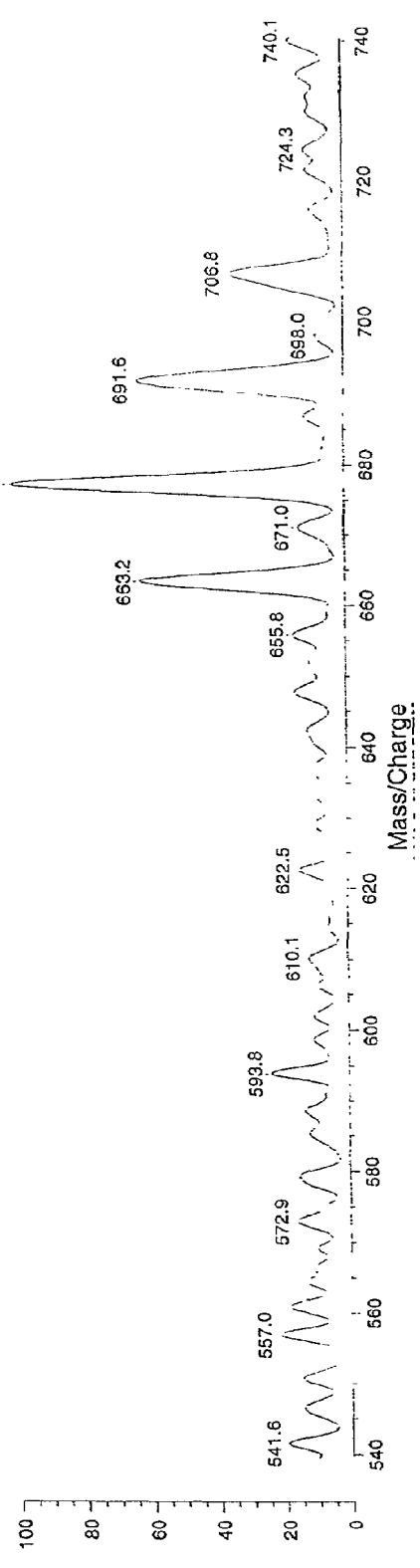
Figure 22:
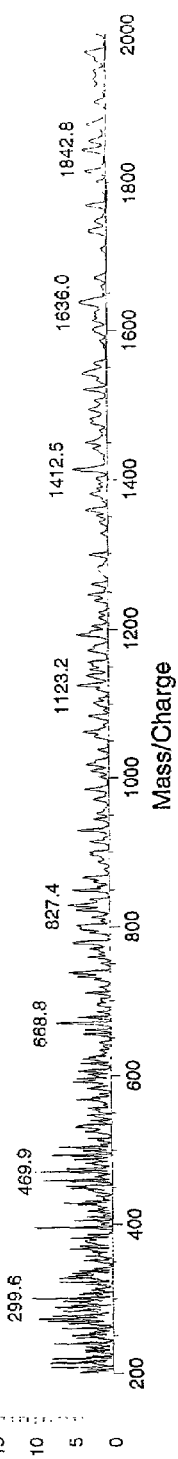
FIG. 22 is a spectrum generated by mass spectrometry of a control sample corresponding with the further sample of the sixth example.
Figure 23:
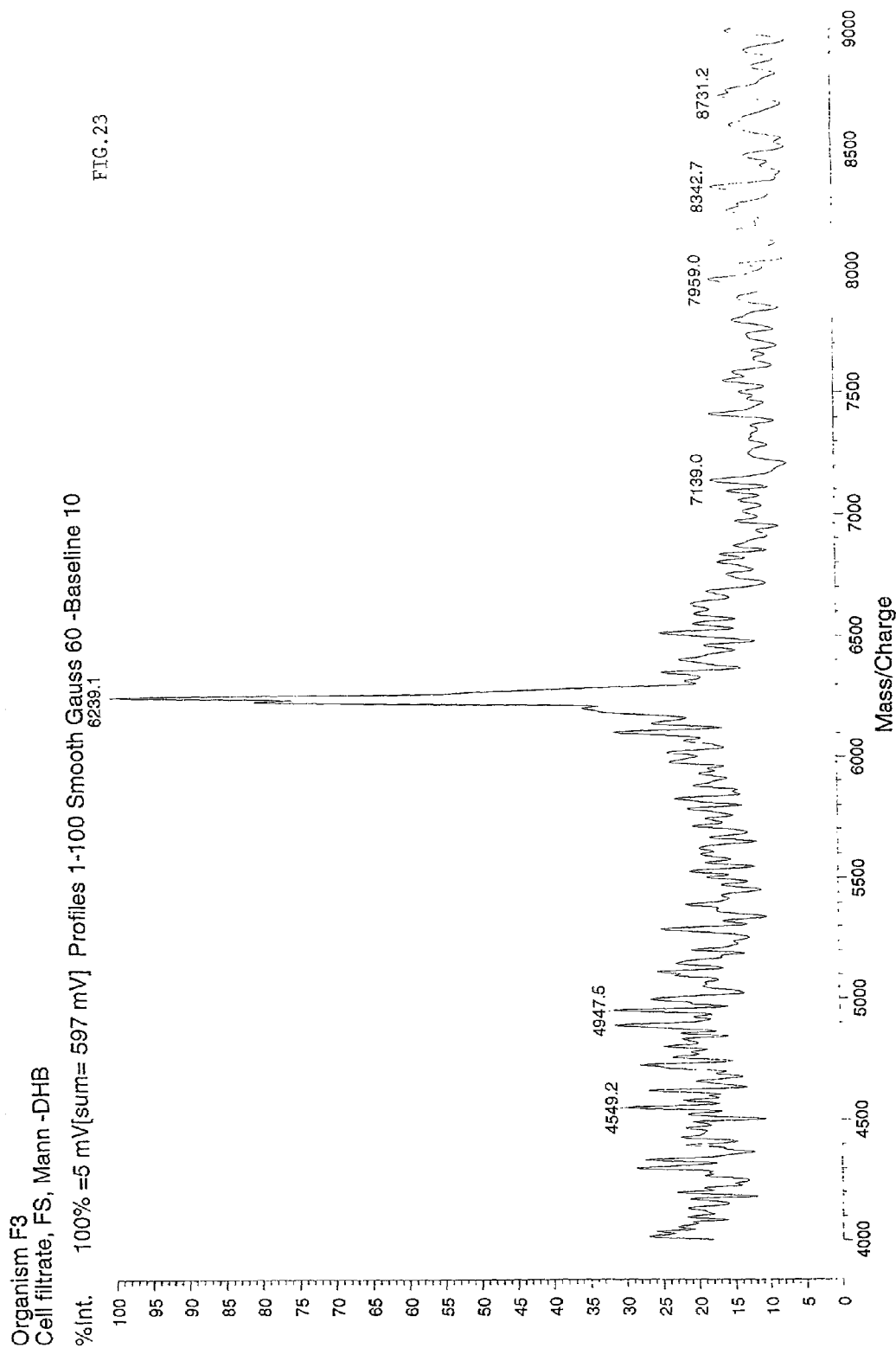
FIG. 23 is a spectrum generated by mass spectrometry of a sample generated in a seventh example in accordance with the invention.

FIG. 16 illustrates the vessel 228 in further detail. The apparatus of FIG. 15 can be used to generate mycelial biomass in the same manner as is described in relation to FIG. 12. Moreover, the apparatus can be used to stimulate secondary metabolism. FIG. 17 illustrates an arrangement whereby the apparatus is being used with replacement medium 220 to stimulate such secondary metabolism. In this case, since the membranes 234, 236 extends substantially longitudinally of the vessel 228, the apparatus 200 can be laid horizontally to achieve full contact of secondary medium 220 with the membranes 234, 236. This can be advantageous since the apparatus can be stored on a simple rack. The dam 229 prevents ingress of liquid into the vessel 228 when in the horizontal position.

Although the apparatus 200 is shown in a horizontal position in FIG. 16, in practice it is unlikely that the quantity of liquid in the receptacle 210 will be exactly the amount to produce the arrangement illustrated in FIG. 16. However, the orientation of the apparatus can be deviated slightly from the horizontal in order to achieve as much contact as possible between the membranes 234, 236 and the secondary medium 220.

In each of the embodiments described in FIGS. 12 to 17, it is clear that the microorganism is isolated from the exterior of the fermentation vessel 128, 228, so that spores generated by the microorganism cannot pass into the medium contained in the receptacle 110, 210. Accordingly, secondary metabolites introduced into secondary medium 120, 220 are separated from the biomass by which they are produced.

By virtue of the isolation, and the definition of an inner chamber within the vessel 128, 228, a pressure differential can be created across the membrane 132, 232 so as to urge medium therethrough. By controlling the pressure differential, or another mechanism such as humidity gradient, the rate at which medium is supplied to the microorganism can be controlled, thereby allowing the control of metabolism, growth and cellular differentiation.

It will be appreciated that in the embodiments illustrated in FIGS. 12 to 16, the outer membrane 134 can be augmented or replaced by an outer polypropylene sheet, with pore size up to 0.3 microns. Such a sheet 134, 234 would be capable of preventing biomass transfer out of the vessel into the medium contained on the receptacle. In practice, a vessel constructed in that way would still be capable of presenting medium to a microorganism inoculated on the inner membrane 136, since medium would soak through the polypropylene sheet by virtue of pressure differential, humidity gradient, or both mechanisms. Thereafter, medium which has soaked through will wick up the inner membrane 136, 236 to the microorganism.

Figure 24:
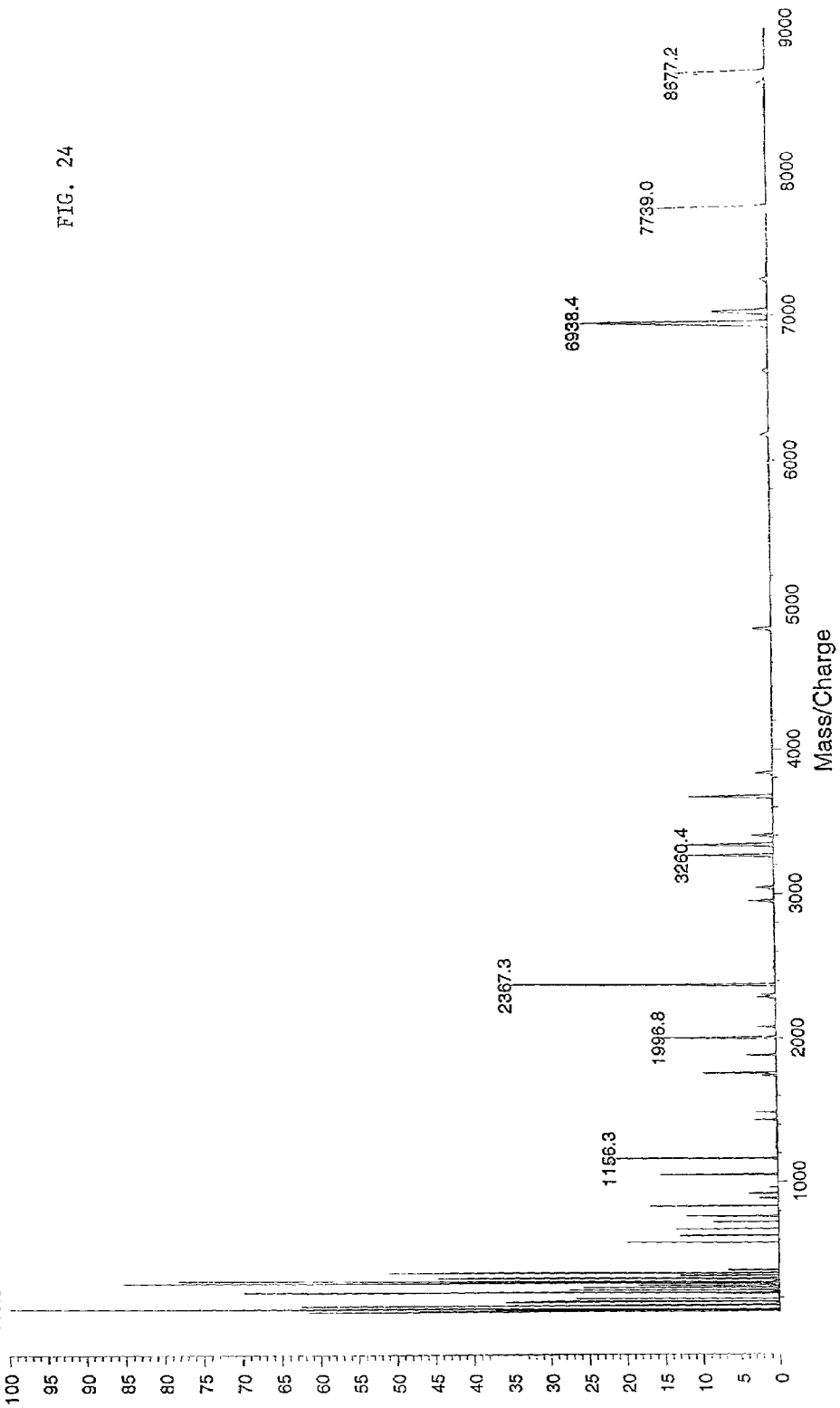
FIG. 24 is a spectrum generated by mass spectrometry of a control sample corresponding with the sample whose spectrum is illustrated in FIG. 23.

It will be apparent that the invention is not limited to vessels 128, 228 described above. For example, FIG. 18 illustrates a component 300 comprising a wicking material with substantial rigidity, which could be used as a fermentation vessel in the apparatus previously described. In that component, microorganism could be allowed to grow over the entire internal surface area of the component 300, thus maximising the biomass thereof.

A further demonstration of the nutrient replacement technique to substantially remove growth medium components and enable the direct detection of secreted secondary metabolites by MALDI-TOF mass spectrometry is demonstrated in the following sixth example of use of the apparatus, with reference to FIGS. 17 to 20 of the drawings.

Two unidentified fungi F1 and F2 are used in the example. For the purpose of the example, organism F1 is known to produce a family of metabolites called verticillins while F2 is known to produce another family of metabolites called enniatins.

Both organisms are grown in a fermentation apparatus 100 as illustrated in FIG. 14, under previously described conditions for fungi using FS as the growth medium and the crystalline sugar mannitol (10 g/l) as the replacement medium. In the apparatus, a precise volume of medium (25 ml) is placed in contact with the maximum surface area of the membrane, as shown in that drawing. The membranes 134, 136 are replaced by a single membrane constructed from hydrophilic polypropylene fibre (Kimberly-Clark) with an open structure which acts to support organism growth but not physically prevent penetration. In each case, the apparatus is inoculated using an agar plug containing actively growing mycelium. The growth phase FS is maintained for 10 days and then incubation of the replacement medium is allowed to proceed for 10 days. The temperature under both phases of growth is controlled at 22° C.

Despite penetration of the membrane support to the medium side, both fungi remain almost entirely attached, facilitating easy aseptic transfer to a second vessel containing the replacement medium. The fungal mycelium remains attached to the membrane support while incubated on the replacement medium allowing easy separation from the fungal biomass at the end of incubation. The nutrient replacement medium containing secreted fungal metabolites is retained for analysis.

In control experiments run alongside the above described example for reasons of composition, the organisms are allowed to grow on FS medium with no medium replacement, for a period of 20 days. A sample of the FS medium free of any fungal mycelium is retained for analysis.

Experimental and control samples are then analysed by MALDI-TOF mass spectrometry as follows:

300 μl of the experimental samples are dried down under vacuum and concentrated threefold by resuspending in 100 μl 50% methanol in deionised water containing 0.1% trifluoroacetic acid. The aqueous control samples are analysed directly without the concentration step. 0.5 μl of sample is mixed with 0.5 μl of matrix (20 mg/ml 2,5-dihydroxybenzoic acid in deionised water) on a mass spectrometer slide and allowed to dry. The slide is then inserted into the instrument. The mass spectrometer is operated in reflectron mode with an extraction voltage of 40 kV. The laser is tuned to an optimal level for the analysis of each sample.

In the spectra of the experimental samples, peaks corresponding to the verticillins (organism F1) are prominent and clearly identifiable (FIG. 19*a*). A fragment of the particular area of interest of FIG. 19*a* is expanded in FIG. 19*b*.

For example, a peak which is prominent in FIG. 19*b*, has a mass/charge ratio of 755.5 corresponds with verticillin B, potassium adduct ($M_B$+3H+$K^+$). Another peak, prominent at a mass/charge ratio of 771.1 corresponds with verticillin C, sodium adduct ($M_C$+3H+$Na^+$). These correspondences are provided in libraries of data which are in the public domain.

Similarly, the experimental samples generated from organism F2 are analysed by MALDI-TOF mass spectrometry and identify members of the enniatin family. These are shown in the spectra illustrated in FIGS. 21*a* and 21*b*.

As shown in FIG. 21*b*, a peak is prominent at a mass/charge ratio of 663.2. This corresponds with enniatin B, sodium adduct ($M_B$+$Na^+$). A peak at mass/charge ratio 677.1 corresponds with enniatin B, potassium adduct ($M_B$+$K^+$), a peak at 691.6 corresponds with enniatin D, potassium adduct ($M_D$+$K^+$) and a peak at mass/charge ratio of 706.8 corresponds with enniatin A, sodium adduct ($M_A$+2H+$Na^+$).

The corresponding control samples (FIG. 20 for F1 and FIG. 22 for F2) generate very poor spectra under MALDI-TOF mass spectrometry. In these spectra, there is no evidence of a peak corresponding to either of the verticillin (FIG. 20) or the enniatin (FIG. 22) species identified in respect of the experimental samples.

For optimal results in applying MALDI-TOF mass spectrometry to a sample, it is desirable that the sample crystallises with the matrix on the slide prior to analysis. Crystallinity is not apparent on the slides containing control samples which explains the poor analytical results. This problem arises from the higher concentrations of medium components in each control sample, which cause a syrup to be formed when the control sample is dehydrated.

It can be seen from the foregoing example that the nutrient replacement process clearly generates samples of fungal origin which can be analysed directly by MALDI-TOF mass spectrometry without extensive pre-preparation.

A further example will now be used to demonstrate that the procedures and apparatus are applicable to the secretion of proteins into a "clean" medium, allowing for ease of isolation. In this example, another unidentified fungus, F3 is grown under identical conditions as F1 and F2 and experimental and control samples analysed by MALDI-TOF mass spectrometry. The spectrum corresponding to the experimental sample is illustrated in FIG. 23, and that corresponding to the control sample is illustrated in FIG. 24. In the experimental samples, a characteristic peak corresponding to a small unidentified protein with an m/z (mass/charge ratio) of 6239.1 is clearly visible (FIG. 23). Again, the corresponding control spectrum shown in FIG. 24 is poor and no protein peaks are detectable.

The nutrient replacement process therefore provides a means of culturing organisms to produce samples containing secreted proteins which can be detected directly by MALDI-TOF mass spectrometry (a technology used extensively for protein and peptide analysis).

Combining the nutrient replacement process with MALDI-TOF analysis therefore enables the direct screening of organisms for secreted protein products. The organisms may be wild type strains or genetically modified by the insertion of a gene (expressing a known or unknown protein) into a suitable host. The presently described procedures and apparatus allow such protein expression to be conducted and analysis to be applied directly to the generated samples, without the need for intermediate steps to increase the purity or cleanness of the sample. Purity and cleanness are concerned with the level of impurities in the sample—the concentration of the desired biochemical in the sample is of less importance than the need to ensure that other chemicals do not prevent operation of or obscure the spectrum of the chemical or chemicals under investigation.

Once metabolites have been produced by the methods described above in accordance with the apparatus illustrated in the accompanying drawings, they can be isolated and prepared in accordance with known methods to produce pharmaceuticals for medical or veterinary use, or to produce agrochemicals such as fungicides or other pesticides. Moreover, the metabolites can be extracted to establish their chemical structures, as a precursor to identify alternative methods of production thereof, such as by non-biological chemical processes.

In particular, samples of secondary metabolites can be produced by methods as described above in accordance with specific embodiments of inventions, for development of new biochemicals, such as pharmaceuticals (both medical and veterinary) and agrochemicals (e.g. pesticides, fungicides, herbicides and growth regulators). A large array of different metabolites can be produced with ease. Each metabolite can then be tested for efficacy, for instance as a pharmaceutical or agrochemical, and any metabolites demonstrating useful effects can then be selected for further development. Further development includes the steps of identifying a method by which metabolite can be produced for commercial exploitation thereof. This may be by large scale fermentation in accordance with the described procedures, or alternatively it could involve identifying the molecular structure of a metabolite so that it can be synthesised.

It will be appreciated by the reader that the term metabolite is being used in its broadest sense, i.e. a biochemical the product of a biosynthesis process within, or associated with, a microorganism. In that sense, a metabolite would include one of the secondary products associated with metabolism in a fungus, and may also include metabolic products such as enzymes, proteins and peptides.

What is claimed is:

1. A method of producing a biochemical, comprising the steps of:
   inoculating with a microorganism a first face of a support means forming a dividing partition defining first and second volumes of a container, said first volume being in communication with the ambient atmosphere via a gas permeable plug;
   mounting said support means to said container with said first face of the support means exposed to said first volume and isolated from said second volume;
   supplying to said second volume a first liquid medium providing conditions for growth of said microorganism;
   allowing access to said first liquid medium by said microorganism;
   allowing said microorganism to grow at the air/first liquid medium interface;
   ending access of said microorganism to said first liquid medium and separating said microorganism therefrom by removing a portion of the container which contains said first liquid medium;
   attaching to said container a replacement for said removed portion;
   supplying to said second volume a second liquid medium providing conditions for biosynthesis of said biochemical by said microorganism;
   allowing access to said second liquid medium by said microorganism, and
   allowing said microorganism to produce said biochemical in its cells or to secrete said biochemical into said second liquid medium, or both.

2. A method according to claim 1 wherein the second medium provides conditions for a secondary metabolism pathway to be established, said biochemical being a secondary metabolite of said microorganism.

3. A method according to claim 1 including the step of extracting said biochemical from said second medium.

4. A method according to claim 1 including the step of extracting said biochemical from biomass of said microorganism.

5. A method according to claim 3 including the step of separating said biochemical from an extract the product of said extracting step.

6. A method according to claim 5 wherein the step of separating said biochemical includes performing high pressure liquid chromatography on said extract.

7. A method according to claim 1 including the step of controlling delivery of said first medium to said microorganism when said microorganism has access thereto.

8. A method according to claim 7 wherein said step of controlling delivery of said first medium includes the step of regulating a pressure gradient along which said first medium is delivered.

9. A method according to claim 7 wherein said step of controlling delivery of said first medium includes the step of regulating a humidity gradient along which said first medium is delivered.

10. A method according to claim 7 wherein said step of controlling delivery of said first medium includes the step of regulating a concentration gradient along which said first medium is delivered.

11. A method according to claim 1 including the step of controlling delivery of said second medium to said microorganism when said microorganism has access thereto.

12. A method according to claim 11 wherein said step of controlling delivery of said second medium includes the step of regulating a pressure gradient along which said second medium is delivered.

13. A method according to claim 11 wherein said step of controlling delivery of said second medium includes the step of regulating a humidity gradient along which said second medium is delivered.

14. A method according to claim 11 wherein said step of controlling delivery of said second medium includes the step of regulating a concentration gradient along which said second medium is delivered.

* * * * *